(12) United States Patent
van Dam et al.

(10) Patent No.: US 11,398,311 B2
(45) Date of Patent: *Jul. 26, 2022

(54) SYSTEM FOR VISUALIZING HEART ACTIVATION

(71) Applicant: Peacs Investments B.V., Nieuwerbrug aan den Rijn (NL)

(72) Inventors: Peter Michael van Dam, Nieuwerbrug aan den Rijn (NL); Eelco Mattias van Dam, Nieuwerbrug aan den Rijn (NL)

(73) Assignee: PEACS INVESTMENTS B.V., Nieuwerbrug aan den Rijn (NL)

( * ) Notice: Subject to any disclaimer, the term of this patent is extended or adjusted under 35 U.S.C. 154(b) by 944 days.

This patent is subject to a terminal disclaimer.

(21) Appl. No.: 15/742,856

(22) PCT Filed: Jul. 11, 2016

(86) PCT No.: PCT/EP2016/066424
§ 371 (c)(1),
(2) Date: Jan. 8, 2018

(87) PCT Pub. No.: WO2017/005933
PCT Pub. Date: Jan. 12, 2017

(65) Prior Publication Data
US 2018/0233232 A1    Aug. 16, 2018

Related U.S. Application Data

(63) Continuation of application No. 14/795,670, filed on Jul. 9, 2015, now Pat. No. 11,289,207.

(51) Int. Cl.
| | |
|---|---|
| *G06G 7/48* | (2006.01) |
| *G16H 50/50* | (2018.01) |
| *G06T 17/20* | (2006.01) |
| *G06T 19/20* | (2011.01) |
| *A61B 5/316* | (2021.01) |
| *A61B 5/318* | (2021.01) |
| *G16Z 99/00* | (2019.01) |
| *A61B 34/10* | (2016.01) |
| *A61B 6/00* | (2006.01) |
| *A61B 5/00* | (2006.01) |
| *A61B 5/055* | (2006.01) |
| *A61B 5/287* | (2021.01) |

(52) U.S. Cl.
CPC .............. *G16H 50/50* (2018.01); *A61B 5/316* (2021.01); *A61B 5/318* (2021.01); *G06T 17/20* (2013.01); *G06T 19/20* (2013.01); *G16Z 99/00* (2019.02); *A61B 5/0044* (2013.01); *A61B 5/055* (2013.01); *A61B 5/287* (2021.01); *A61B 6/503* (2013.01); *A61B 6/5247* (2013.01); *A61B 2034/104* (2016.02)

(58) Field of Classification Search
None
See application file for complete search history.

(56) References Cited

U.S. PATENT DOCUMENTS

| | | |
|---|---|---|
| 5,657,755 A | 8/1997 | Desai |
| 6,575,659 B1 | 6/2003 | Valtwies et al. |
| 6,575,969 B1 | 6/2003 | Rittman, III et al. |
| 7,155,042 B1 | 12/2006 | Cowan et al. |
| 7,382,907 B2 | 6/2008 | Luo et al. |
| 7,787,951 B1 | 8/2010 | Min |
| 7,860,558 B2 | 12/2010 | Feild et al. |
| 8,155,739 B2 | 4/2012 | Keel et al. |
| 8,326,419 B2 | 12/2012 | Rosenberg et al. |
| 8,478,388 B2 | 7/2013 | Nguyen et al. |
| 8,615,298 B2 | 12/2013 | Ghosh et al. |
| 9,078,573 B2 | 7/2015 | Ramanathan et al. |

(Continued)

FOREIGN PATENT DOCUMENTS

| | | |
|---|---|---|
| CN | 1901836 A | 1/2007 |
| CN | 101828915 A | 9/2010 |

(Continued)

OTHER PUBLICATIONS

Hsiao, Chia-Hung, and Tsair Kao. "Constructing a 3-D mesh model for electrical cardiac activity simulation." Computers and biomedical research 33.1 (2000): 23-42.*

Deng, Dongdong, Junjie Zhang, and Ling Xia. "Three-dimensional mesh generation for human heart model." Life System Modeling and Intelligent Computing. Springer, Berlin, Heidelberg, 2010. 157-162.*

Prener et al. "Physiological Range of Mechanical Synchronicity of the Human Heart: Comparison Between Different Echocardiographic Assessment Modalities" (Ultrasound in Med. and Biol., vol. 31 (2005) pp. 1163-1172).*

Lie, Knut-Andreas, et al. "Open-source MATLAB implementation of consistent discretisations on complex grids." Computational Geosciences 16.2 (2012): 297-322.*

(Continued)

*Primary Examiner* — Anna Skibinsky
(74) *Attorney, Agent, or Firm* — Foley & Lardner LLP

(57) ABSTRACT

The invention relates to a method and a system for providing a representation of synchronicity of electrical activation of heart tissue. The method includes obtaining a three-dimensional model of electrical activation of the heart. The three-dimensional model includes a mesh with a plurality of nodes, each node having associated therewith a time delay between stimulation of the heart at a stimulation site and activation of the heart at that respective node. For each node a stimulus site is defined at the location of that node. For each node a modified three-dimensional model of electrical activation of the heart resulting from stimulation at that node is determined. For each node a measure for heart activation synchronicity for the heart based on stimulation at that node is determined A heart synchronicity map is determined representing a three-dimensional model of the heart, indicating at each node the respective measure for heart activation synchronicity.

21 Claims, 10 Drawing Sheets
(9 of 10 Drawing Sheet(s) Filed in Color)

(56) References Cited

U.S. PATENT DOCUMENTS

| | | |
|---|---|---|
| 9,155,897 B2 | 10/2015 | Ghosh et al. |
| 9,265,951 B2 | 2/2016 | Sweeney |
| 9,278,219 B2 | 3/2016 | Ghosh |
| 9,381,363 B2 | 7/2016 | Ryu et al. |
| 9,439,578 B2 | 9/2016 | Thakur et al. |
| 9,510,763 B2 | 12/2016 | Ghosh et al. |
| 9,579,064 B2 | 2/2017 | Kovtun et al. |
| 9,586,052 B2 | 3/2017 | Gillberg et al. |
| 9,681,817 B2 | 6/2017 | Maskara et al. |
| 9,875,544 B2 | 1/2018 | Rai et al. |
| 9,877,789 B2 | 1/2018 | Ghosh |
| 9,986,928 B2 | 6/2018 | Gillberg et al. |
| 10,016,145 B2 | 7/2018 | Thakur et al. |
| 10,369,358 B2 | 8/2019 | Monteiro |
| 10,471,263 B2 | 11/2019 | Pacheco |
| 10,713,790 B2 | 7/2020 | Adler |
| 10,932,863 B2 | 3/2021 | Adler |
| 2002/0105516 A1 | 8/2002 | Tracy |
| 2002/0128565 A1 | 9/2002 | Rudy |
| 2005/0096515 A1 | 5/2005 | Geng |
| 2005/0096522 A1 | 5/2005 | Reddy et al. |
| 2006/0079759 A1 | 4/2006 | Vaillant et al. |
| 2006/0224071 A1 | 10/2006 | Stewart |
| 2007/0270703 A1 | 11/2007 | He et al. |
| 2008/0205716 A1 | 8/2008 | Von Berg et al. |
| 2009/0088655 A1 | 4/2009 | Vajdic et al. |
| 2009/0099619 A1 | 4/2009 | Lessmeier et al. |
| 2009/0099679 A1 | 4/2009 | Sandoval et al. |
| 2009/0287087 A1 | 11/2009 | Gwerder et al. |
| 2010/0070249 A1* | 3/2010 | Ionasec ............... G06F 19/321 703/2 |
| 2010/0160773 A1 | 6/2010 | Cohen et al. |
| 2010/0268059 A1 | 10/2010 | Ryu et al. |
| 2010/0280399 A1 | 11/2010 | Francis et al. |
| 2010/0312100 A1 | 12/2010 | Zarkh et al. |
| 2011/0060576 A1* | 3/2011 | Sharma ............... G06T 7/0012 703/11 |
| 2011/0071583 A1 | 3/2011 | Muntendam |
| 2012/0061612 A1 | 3/2012 | Yoshioka et al. |
| 2012/0157822 A1 | 6/2012 | Van Dam et al. |
| 2012/0230565 A1 | 9/2012 | Steinberg et al. |
| 2012/0235993 A1 | 9/2012 | Kim |
| 2012/0283587 A1 | 11/2012 | Gosh et al. |
| 2013/0060315 A1 | 3/2013 | Elghazzawi et al. |
| 2013/0116533 A1 | 5/2013 | Lian et al. |
| 2013/0177223 A1 | 7/2013 | Lee et al. |
| 2013/0184697 A1 | 7/2013 | Han et al. |
| 2013/0197881 A1* | 8/2013 | Mansi ............... A61N 1/3627 703/2 |
| 2013/0245473 A1 | 9/2013 | Ramanathan et al. |
| 2013/0304407 A1 | 11/2013 | George et al. |
| 2014/0088943 A1 | 3/2014 | Trayanova et al. |
| 2014/0107510 A1 | 4/2014 | Bogun et al. |
| 2014/0121636 A1 | 5/2014 | Boyden et al. |
| 2014/0194760 A1 | 7/2014 | Albert |
| 2014/0207005 A1 | 7/2014 | Bukkapatnam et al. |
| 2014/0371807 A1 | 12/2014 | Ghosh et al. |
| 2015/0170978 A1 | 6/2015 | Chen et al. |
| 2015/0294082 A1 | 10/2015 | Passerini et al. |
| 2015/0356742 A1 | 12/2015 | Barbarito et al. |
| 2016/0331261 A1 | 11/2016 | Someya et al. |
| 2016/0342761 A1 | 11/2016 | Whiting et al. |
| 2016/0345833 A1 | 12/2016 | Adams |
| 2017/0011197 A1 | 1/2017 | Van Dam et al. |
| 2017/0071492 A1 | 3/2017 | Van Dam et al. |
| 2017/0071675 A1 | 3/2017 | Dawoud et al. |
| 2017/0178403 A1 | 6/2017 | Krummen et al. |
| 2017/0209698 A1 | 7/2017 | Villongco et al. |
| 2018/0064947 A1 | 3/2018 | Pacheco et al. |
| 2018/0303345 A1 | 10/2018 | Adler |
| 2019/0038357 A1 | 2/2019 | Adler |
| 2019/0111265 A1 | 4/2019 | Zhou |
| 2020/0029817 A1 | 1/2020 | Adler |
| 2020/0061383 A1 | 2/2020 | Yomtov et al. |

FOREIGN PATENT DOCUMENTS

| | | |
|---|---|---|
| EP | 2 675 354 A4 | 12/2013 |
| WO | WO-2009/129475 A1 | 10/2009 |
| WO | WO-2012/061612 A2 | 5/2012 |
| WO | WO-2013/006713 A2 | 1/2013 |
| WO | WO-2015/170978 A1 | 11/2015 |

OTHER PUBLICATIONS

Romero, Daniel, et al. "Effects of the purkinje system and cardiac geometry on biventricular pacing: a model study." Annals of biomedical engineering 38.4 (2010): 1388-1398.*

International Search Report and Written Opinion, PCT/EP2016/066424, Peacs B.V., 10 pages (dated Jul. 28, 2017).

Geselowitz, David B., "Description of Cardiac Sources in Anisotropic Cardiac Muscle: Application of Bidomain Model," Journal of Electrocardiology, vol. 25, 1992, pp. 65-67.

Geselowitz, David B., "On the Theory of the Electrocardiogram," Proceedings of the IEEE, vol. 77, No. 6, Jun. 1989, pp. 857-876.

Han et al., Enhanced Computer Vision, Microsoft Kinect Sensor: A Review, IEEE Transactions on Systems, Man and Cybernetics, Part B, IEEE Transactions on Cybernetics, vol. 43, No. 5, Oct. 2013, pp. 1318-1334.

Huiskamp et al., "Heart Position and Orientation in Forward and Inverse Electrocardiography," Med Biol Eng Comput 30, 1992, 8 pages.

Huiskamp et al., The depolarization sequence of the human heart surface computed from measured body surface potentials. IEEE Transactions on Biomedical Engineering. Dec. 1988;35(12): pp. 1047-1058. PubMed PMID: 3220498.

Mahmoud et al., "Interhospital Transfer Due to Failed Prehospital Diagnosis for Primary Percutaneous Coronary Intervention: an Observational Study on Incidence, Predictors, and Clinical Impact," European Heart Journal: Acute Cardiovascular Care 2(2), 2013, pp. 166-175.

Meijs et al., On the Numerical Accuracy of the Boundary Element Method. IEEE Transactions on Biomedical Engineering, Oct. 1989;BME-36, vol. 10, pp. 1038-1049.

Oostendorp et al., Interpolation on a triangulated 3D surface. Journal of Computational Physics. 1989;80(2): pp. 331-343.

Poerner et al., "Physiological Range of Mechanical Synchronicity of the Human Heart: Comparison Between Different Echocardiographic Assessment Modalities," Ultrasound in Med. and Biol., vol. 31, 2005, pp. 1163-1172.

Prassl et al., "Automatically Generated, Anatomically Accurate Meshes for Cardiac Electrophysiology Problems," (IEEE Transactions on Biomedical Engineering), vol. 56, 2009, pp. 1318-1330.

Rantner et al., "Placement of implantable cardioverter-defibrillators in paediatric and congenital heart defect patients: a pipeline for model generation and simulation prediction of optimal configurations," J. Physiol, vol. 591, 2013, pp. 4321-4334.

Swihart et al., Numerical Methods for solving the forward problem in electrocardiography, The Theoretical Basis of Electrocardiology, Nelson CV, Geselowitz DB, editors. Oxford: Clarendon Press; 1976, pp. 257-293.

Van Dam et al., "A New 3D Patient Specific Morphing Tool Enabling Clinical Application of Non-Invasive Cardiac Activation Imaging," 2012, 1 page.

Van Dam et al., "Application of the Fastest Route Algorithm in the Interactive Simulation of the Effect of Local Ischemia on the ECG," Med Biol Eng Comput 47, Published online Sep. 3, 2008, 10 pages.

Van Dam et al., "Non-Invasive Imaging of Cardiac Activation and Recovery," Annals of Biomedical Engineering, vol. 37, No. 9, Sep. 2009, pp. 1739-1756.

Van Dam et al., "Quantitative Localization of Premature Ventricular Contractions Using Myocardial Activation ECGI from the Standard 12-Lead Electrocardiogram," Journal of Electrocardiology, vol. 46, 2013, pp. 574-579.

Van Oosterom, A., "Genesis of the T Wave as Based on an Equivalent Surface Source Model," Journal of Electrocardiology, vol. 34S, 2001, pp. 217-227.

(56) References Cited

OTHER PUBLICATIONS

Van Oosterom, A., "The Equivalent Double Layer: Source Models for Repolarization," Comprehensive Physiology. Springer-Verlag London Limited, 2010, pp. 227-246.
Van Oosterom, et al., The Influence of Heart Position and Orientation on Body Surface Potentials. Journal of Electrocardiology vol. 24, No. 3, Jul. 1991, 3 pages.
Van Oosterom, The Equivalent Surface Source Model in its Application to the T Wave, Journal of Electrocardiology '01; 2002: Univ Press São Paolo, 6 pages.
Wilson et al., "The Distribution of the Action Currents Produced by Heart Muscle and Other Excitable Tissues Immersed in Extensive Conducting Media," The Journal of General Physiology, Published Jan. 20, 1933, pp. 423-456.
"12 Lead ECG Placement example," YouTube video, published Feb. 18, 2015 [retrieved on Oct. 23, 2018], Retrieved from the Internet:<URL:https://www.youtube.com/watch?v=0gAOy7f2-Gs>.
Lieberman, "Interpreting 12-Lead ECGs: A Piece by Piece Analysis" The Nurse Practitioner, vol. 33 (2008) pp. 28-35.
Zalenski et al., "Value of Posterior and Right Ventricular Leads in Comparison to the Standard 12-Lead Electrocardiogram in Evaluation of ST-Segment Elevation in Suspected Acute Myocardial Infarction" The American Journal of Cardiology, vol. 79, Issue 12, Jun. 15, 1997, pp. 1579-1585.
Van Dam et al., "New Computer Program for detecting 12 Lead ECG Misplacement using a 3D Kinect Camera," Computing in Cardiology, vol. 40, 2013, pp. 1175-1178.
Zhang et al., "3-Dimensional Activation Sequence Reconstruction from Body Surface Potential Maps by Means of a Heart-Model-Based Imaging Approach," Computers in Cardiology, vol. 31, 2004, pp. 1-4.
Fitzpatrick et al., "Handbook of Medical Imaging, vol. 2. Medical Image Processing and Analysis." Dec. 31, 2000, Chapter 8, pp. 449-445.
Franzone, Piero Colli, et al. "Spread of excitation in 3-D models of the anisotropic cardiac tissue. II. Effects of fiber architecture and ventricular geometry." Mathematical biosciences 147.2 (1998): 131-171.
Romero et al. "Effects of the Purkinje System and Cardiac Geometry on Biventricular Pacing: A Model Study," Annals of Biomedical Engineering, vol. 38, No. 4, Apr. 2010 (2010) pp. 1388-1398.
Tianming et al., "Deformable registration of cortical structuresvia hybrid volumetric and surface warping." Neuroimage. Aug. 2004, vol. 22, No. 4, pp. 1790-1801.
Zhou et al., "Voxel-conding for tiling complex volumetric objects." In Proceedings the Eighth Pacific Conference on Computer Graphics and Applications. Oct. 3, 2000, pp. 307-451.
Copending U.S. Appl. No. 17/174,308, Inventor: Barry Yomtov, Title: "Method of Providing Ventricular Arrythmia Localization and Myocardium Wall Thickness Within a 3D Heart Model," filed Feb. 11, 2021.
Copending U.S. Appl. No. 17/174,328, Inventor: Barry Yomtov, Title: "Method of Providing Ventricular Arrhythmia Localization with a Heart Model Derived from Machine Learning," filed Feb. 11, 2021.
Daubert, et al., "Avoiding non-responders to cardiac resynchronization therapy: a practical guide", European Heart Journal Advance Access, European Heart Journal, doi:10.1093/eurheartj/ehw270, 13 pages, (Jul. 1, 2016).
Hoppe, "Introduction to Network Mathematics," 2007-2008 [online ][retrieved, on Jul. 1, 2021] Retrieved from the Internet <URL: htt://eds hare .so ton .ac .uk/922/2/i ndex.html >.
International Bureau, International Preliminary Reporton Patentability dated Mar. 12, 2019 for International Application No. PCT/US2017/050188, 9 pages.
International Preliminary Report on Patentability for counterpart Application No. PCT/US2018/044746, dated Feb. 13, 2020.
International Preliminary Report on Patentability for counterpart Application No. PCT/US2019/043900, dated Feb. 11, 2021.
International Search Report and the Written Opinion of the International Searching Authority for International Application No. PCT/US2020/045764, dated Nov. 17, 2020, 13 pages.
International Search Report and the Written Opinion of the International Searching Authority from the European Patent Office in Application No. PCT/US2017/050188 dated Nov. 7, 2017.
International Search Report and the Written Opinion of the International Searching Authority from the European Patent Office in Application No. PCT/US2017/050188 dated Nov. 7, 2017, 17 pages.
International Search Report and Written Opinion for counterpart Application No. PCT/US2018/044746, dated Jan. 28, 2019.
International Search Report and Written Opinion for counterpart Application No. PCT/US2019/043900, dated Nov. 20, 2019.
Noheria, et al., "Ablating Premature Ventricular Complexes: Justification, Techniques, and Outcomes," MDCVJ | XI (2), houstonmethodist.org/debakey-journal, 2015, pp. 109-120.
Non-Final Office Action on U.S. Appl. No. 14/795,670 dated Jul. 7, 2021.
Notice of Allowance on U.S. Appl. No. 15/343,542 dated Jul. 14, 2021.
Padeletti, Luigi et al., "Simultaneous his bundle and left ventricular pacing for optimal cardiac resynchronization therapy delivery", Circulation: Arrhythmia and Electrophysiology, 2016, vol. 9, Article No. e003793, pp. 1-8.
Ploux, et al., "Noninvasive Electrocardiographic Mapping to Improve Patient Selection for Cardiac Resynchronization Therapy", Cardiac Resynchronization, Journal of the American College of Cardiology, vol. 61, No. 24, ISSN 00735-1097, 9 pages, (2013).
Schulze, Walther et al., "Automatic camera-based identification and 3-D reconstruction of electrode positions in electrocardiographic imaging," Biomed. Eng.-Biomed, Tech, 59(6): 2014, pp. 515-528.
Vijayaraman, Pugazhendhi et al., "His-optimized cardiac resynchronization therapy to maximize electrical resynchronization", Circulation: Arrhythmia and Electrophysiology, Feb. 2019, vol. 12, Article No. e006934, pp. 1-9.

\* cited by examiner

SYSTEM FOR VISUALIZING HEART ACTIVATION

CROSS-REFERENCE TO RELATED APPLICATIONS

This application is a national stage application of PCT/EP2016/066424 filed on Jul. 11, 2016, which is a continuation of U.S. application Ser. No. 14/795,670 filed Jul. 9, 2015, the entire contents of both are hereby incorporated herein by reference.

FIELD OF THE INVENTION

The present invention relates to visualization of various derived activation parameters of the heart on a 3D heart model. More in particular, the invention relates to providing a representation of synchronicity of electrical activation of heart tissue. Also in particular, the invention relates to virtual pacemaker implantation.

BACKGROUND TO THE INVENTION

Some heart defects in the conduction system result in an asynchronous contraction, conduction disorders, of the heart. As a result the heart does not pump enough blood, resulting ultimately in heart failure. These conduction disorders can have a variety of causes, including age, heart (muscle) damage, medications and genetics.

A common cause for such conduction disorders is a failing part in the left and/or right ventricle fast activation fiber, the His-Purkinje system or scar tissue. Due to this failing part of the His-Purkinje system or blocking scar tissue, the left or right ventricles are not activated in the same, fast way as the other side. This is referred to as Left Bundle Branch Block (LBBB) or Right Bundle Branch Block (RBBB). A known way to improve heart function in case of LBBB or RBBB is implanting a Cardiac Resynchronization Therapy (CRT), also referred to as "biventricular pacing", pacemaker. The electrical stimulated resynchronization of the heart improves the pump function of the heart.

A pacemaker is a medical device that uses electrical impulses, delivered by electrodes, also referred to as leads, contacting the heart muscles, to regulate the beating of the heart. The primary purpose of a pacemaker is to maintain an adequate heart rate resulting in a higher cardiac output. A CRT pacemaker device includes two or more leads of which at least one is located in the right ventricle and one in the left ventricle. These leads can be used to sense the intrinsic, i.e. normal heart driven, activation, or can be used to stimulate, i.e. provoke, an activation at its location.

Cardiac resynchronization can then be achieved by sensing the intrinsic activation in the right ventricle and use this trigger to activate the left ventricle. Alternatively, the entire activation, i.e. left and right ventricle, can be driven by the artificial stimulation, either by improving or by taking over the existing intrinsic activation.

A major issue associated with the use of CRT pacemakers in current clinical practice is finding the optimal pacing lead location within the hearts ventricle chambers. Currently at least thirty percent of the patients with a CRT device implanted do not respond to the CRT therapy. For several years now both the health care system as well as the pacemaker industry is searching for an appropriate easy and reliable guiding method to find these optimal locations

SUMMARY OF THE INVENTION

The invention relates to a computer implemented method for processing measurement data from electrocardiogram, ECG, electrodes on a subject. The method includes obtaining a three-dimensional, 3D, anatomical model of the torso of the subject. Preferably, the anatomical model includes both an outer surface of the torso and positional information on internal structures such as the heart and lungs. The three-dimensional anatomical model of the torso of the subject can e.g. be derived from a medical imaging modality, such as MRI, CT, PET-CT, ultrasound, or the like. The 3D anatomical model can include geometries of the torso, and geometries of one or more of lungs, heart, blood cavities, ribcage, fat and any other relevant tissue in the torso.

The inventors have to date made progress in so called inverse computations where e.g. an activation sequence and/or other parameters of the heart are estimated from surface electrocardiograms.

The inventors devised a Cardiac Isochrone Positioning System (CIPS). CIPS is a non-invasive electrocardiographic imaging (ECGI) method and/or device able to determine the cardiac activation from a, e.g. twelve or more lead, electrocardiogram (ECG). The CIPS model integrates the ECG signals with an MRI or computed Tomography (CT) image derived model of the heart, lungs, and torso in order to compute the positions of cardiac isochrones. Herein, isochrones refer to (virtual) lines drawn on a 3D heart surface model connecting points on this heart model at which the activation occurs or arrives at the same time. The combination of the 3D heart surface model and the isochrones provides a 3D model of activation timing of the heart, herein also referred to as cardiac activation model.

An ECG is defined herein as any method that (preferably non-invasively) correlates actual electrical activity of the heart muscle to measured or derived (electrical activity) of the heart. In case of a classical electrocardiogram the differences in potential between electrodes on the body surface are correlated to the electrical activity of the heart. Derived ECG's can also be obtained in other ways (e.g. by measurement made by a so-called ICD (Implantable Cardioverter Defibrillator)). In order to obtain such a functional image an estimation of the electrical activity has to be provided.

The inventors found that the cardiac activation model can also be used for performing simulations. In particular the cardiac activation model can be used to predict the resulting cardiac activation when a stimulation spot is added to the model.

Therefore according to the invention is provided a computer implemented method for providing a representation of synchronicity of electrical activation of heart tissue. The method includes obtaining a three-dimensional model of electrical activation of the heart. The method may include obtaining a three-dimensional patient-specific model of electrical activation of the heart of a specific patient. The three-dimensional model includes a mesh representing an outer surface of the heart, such as an outer surface of the myocardium. The three dimensional model can include the septal wall. The mesh has a plurality of nodes. Each node has associated therewith a value representative of a time delay between stimulation of the heart at a stimulation site and activation of the heart at that respective node. The method includes for each node of the three-dimensional model of the heart defining a stimulus site at the location of that node in the three-dimensional model of the heart. For each node, on the basis of the three-dimensional model of electrical activation of the heart is determined a modified three-dimensional model of electrical activation of the heart resulting from stimulation at that node. For each node a measure for heart activation synchronicity for the heart is determined based on stimulation at that node. A heart synchronicity map is determined representing a three-dimensional model of the heart, indicating at each node the respective measure for heart activation synchronicity.

Thus, the heart synchronicity map provides an easy overview of synchronicity of activation of the entire heart as a result of activation at a single node, for each node of the 3D heart model. This allows for easy assessment of the impact of activation location.

Optionally, the measure for heart activation synchronicity is one of standard deviation (std) of the depolarization (dep) times of the heart; range in depolarization times; standard deviation of the Left Ventricle (LV) only; delay between stimulus and Septum activation; AV delay; VV delay, etc. The area with the lowest standard deviation of the depolarization times std(dep) can be the best implantation site for a cardiac pacemaker electrode.

Optionally, the method includes defining a common stimulation site, wherein for each node the step of determining the modified three-dimensional model of electrical activation of the heart resulting from stimulation at that node takes into account additional stimulation at the common stimulation location. Thus, the heart synchronicity map provides an easy overview of synchronicity of activation of the entire heart as a result of activation at the common stimulation location and an individual node, for each node of the 3D heart model. This allows for easy assessment of the impact of activation location, for two activation locations. Optionally, the common stimulation site is an intrinsic activation site of the heart. Hence, the heart synchronicity map provides an easy overview of synchronicity of activation of the entire heart as a result of activation at the intrinsic activation site and an individual node, for each node of the 3D heart model. Optionally, the common stimulation site is an artificial stimulation site. Hence, the heart synchronicity map can be used to provide an easy overview of synchronicity of activation of the entire heart as a result of activation at two artificial stimulation sites. It will be appreciated that stimulation at two stimulation locations may be performed simultaneously. Alternatively, it is possible that stimulation at the two locations is not simultaneous. The one stimulation may lag with respect to the other. It will be appreciated that the effect on heart activation synchronicity of the duration of the lag time can be determined as well.

Optionally, the method includes defining a plurality of common stimulation sites, wherein for each node the step of determining the modified three-dimensional model of electrical activation of the heart resulting from stimulation at that node takes into account additional, e.g. simultaneous, stimulation at the plurality of common stimulation sites. Thus, the heart synchronicity map provides an easy overview of synchronicity of activation of the entire heart as a result of, e.g. simultaneous, activation at the plurality of common stimulation sites and an individual node, for each node of the 3D heart model. Optionally, one of the common stimulation sites is an intrinsic activation site of the heart.

Optionally, the three-dimensional model includes a mesh representing the entire outer surface of the heart, such as the entire outer surface of the myocardium, e.g. including the septal wall.

Optionally, the obtaining of the patient-specific three-dimensional model of electrical activation of the heart includes obtaining a patient-specific three-dimensional anatomical model of the heart, and optionally the lungs and the thorax; obtaining ECG data representative of electric function of the heart; and on the basis of the three-dimensional anatomical model of the heart, and optionally the lungs and the thorax, and the ECG data determine the three-dimensional model of electrical activation of the heart. The patient-specific anatomical model can be obtained by medical imaging, such as computer tomography, CT, and/or magnetic resonance imaging, MRI.

Optionally, the three-dimensional anatomical model of the subject is determined by selection from a database. Thereto is provided a database including a plurality of three dimensional anatomical models. The 3D models can include geometries of torsos, optionally including geometries of one or more of lungs, heart, blood cavities, ribcage, fat and any other relevant tissue in the torso. The 3D anatomical models are mutually different. The 3D anatomical models may represent different possible subjects. The 3D anatomical models may e.g. be representative of subjects of different gender, age, weight, body length, chest circumference, frame size, body-mass-index (BMI), etc. The 3D anatomical models may also differ in view of medical criteria, such as blood pressure. It will be appreciated that each 3D anatomical model in the database can e.g. be derived from a medical imaging modality, such as MRI, CT, PET-CT, ultrasound, or the like, from a respective reference subject. It is also possible that some or all 3D anatomical models in the database are fictitious renderings of fictitious reference subjects.

The method can then include selecting, from the plurality of 3D anatomical models in the database, the 3D anatomical model showing closest conformity to the anatomy of the subject. The selection may be made on the basis of parameters, such as gender, age, weight, body length, chest circumference, frame size, BMI, etc. Such selection may be automated on the basis of parameters of the subject that are already known, e.g. from measurements, questions or tests. From a 3D image of the subject several measurements can be computed, e.g. chest circumference, height of the torso etc. These measurements can be used in selecting the appropriate 3D model from the database.

The selection may also be based on visual comparison of the 3D image of the anatomy of the subject with the 3D models in the database. Such selection may be automated on the basis of pattern recognition. This provides the advantage that it is not required to obtain a subject-specific 3D anatomical model for each subject. Instead it is possible to obtain a plurality of different 3D anatomical models and to select a quasi-subject-specific 3D anatomical model that best represents the subject. Optionally, the method includes, after selecting a 3D anatomical model from the database, scaling the 3D anatomical model to the 3D image of the anatomy of the subject, and/or scaling the 3D image to the 3D anatomical model. This enhances conformity of the 3D anatomical model to the 3D image. The 3D anatomical model can be scaled so as to have the outer surface of the 3D anatomical model correspond with the outer surface of the anatomy of the subject as obtained from the 3D image. When the 3D anatomical model is scaled, also dimensions and positions of internal structures such as the lungs and heart can be scaled.

It is also possible to take parameters of the subject into account when scaling the 3D anatomical model. For example, the scaling can be dependent on the amount of body fat and frame size of the subject. In a subject with more body fat, the chest circumference can be larger in relation to the dimensions of heart and lungs, than in a subject with less body fat.

Optionally, the method includes placing a marker on the torso of the subject, for example at the xyphoid. The marker is arranged to be identifiable in the 3D image of the torso of the subject. The marker can be used for determining the position of the heart. The marker at the xyphoid can be used as a reference for the lower end of the heart.

It is also possible to take parameters of the subject into account when determining a position of the heart within the 3D anatomical model. Such parameter can e.g. be weight or age of the subject. The weight can be indicative of a large belly, which pushes the heart upwards. Therefore, a vertical position of the heart in the 3D anatomical model can be modified on the basis of weight of the subject. The heart tends to be positioned more horizontally with increasing age. Therefore, a rotation of the heart in the 3D anatomical model can be modified on the basis of the age of the subject.

Thus, it is possible to provide a good approximation of a subject-specific 3D anatomical model, by selecting an appropriate standard 3D anatomical model from the database. Optionally, the selected 3D anatomical model is scaled to better conform with the 3D image of the anatomy of the subject. Optionally, such scaling of the selected 3D anatomical model involves scaling of the internal structures such as heart and/or lungs. Optionally, a position and/or orientation of the heart in the selected (and optionally scaled) 3D anatomical model is modified on the basis of subject-specific values of one or more parameter such as gender, age, weight, body length, chest circumference, frame size, BMI, etc.

It will be appreciated that the selected, and optionally modified, 3D anatomical model provides a quasi-subject-specific 3D anatomical model that can be used instead of a subject-specific 3D anatomical model. In view of the subject-specific selection the selected, and optionally modified, 3D anatomical model is herein also referred to as subject-specific (or patient-specific) 3D anatomical model.

It will also be possible to only select the internal structures from the database whereas the anatomical model will be derived from the 3D image. The internal structures can then be selected based on subject-specific values of one or more parameters such as gender, age, weight, body length, chest circumference, frame size, BMI, etc. The dimensions, position and orientation of the internal structures, such as heart and/or lungs, can e.g. be selected on the basis of the weight and age of a patient (the heart is more horizontal for older patients or overweighted patients).

Optionally, the obtaining of the three-dimensional model of electrical activation of the heart includes recording the exact locations of electrodes of the ECG on the thorax. It will be appreciated that knowing the exact locations of the electrodes will enhance the accuracy of the three-dimensional model of electrical activation of the heart.

Optionally, the obtaining of the three-dimensional model of electrical activation of the heart includes relating the measurements per electrode of the ECG to the anatomical model of the heart, and optionally the lungs and thorax, and estimating electrical activation of the heart by inverse calculation.

Optionally, the obtaining of the three-dimensional model of electrical activation of the heart includes incorporating scar tissue in the three-dimensional model of the heart. Scar tissue can be simulated in the three-dimensional model of electrical activation by reducing the propagation velocity. Scar tissue can also be accounted for by setting the transition from one node to another to very slow or non-transitional for the areas in the heart wall where scar tissue is present. Incorporating scar tissue can enhance the accuracy of the heart synchronicity mapping. It will be appreciated that the actual location of scar tissue may be obtained from, e.g. the patient-specific anatomical model, from the ECG, or Delayed Enhancement MRI images.

Optionally, the obtaining of the three-dimensional model of electrical activation of the heart includes incorporating blood vessels in the three-dimensional model of the heart. The placement of the blood vessels can be derived from the location of the heart valves and the anatomy and/or model of the heart and/or ventricles. Cardiac blood vessels, or nodes associated with locations of such blood vessels, can also be used as stimulation location. For instance, pacemaker electrodes are sometimes positioned in cardiac blood vessels, such as cardiac veins.

Optionally, the method includes on the basis of the heart synchronicity map determining a node having the highest synchronicity. The node having highest synchronicity can represent the node which, when stimulated, causes the heart to activate with optimum synchronicity. If the synchronicity map is based on synchronization of a single node at any time, the determined node can be a node best suited for artificial stimulation, e.g. an optimum pacemaker electrode location. If the synchronicity map is based on synchronization of one node, e.g. simultaneously, with an intrinsic activation site of the heart, the determined node can be a node best suited for artificial stimulation, e.g. an optimum pacemaker electrode location, in addition to intrinsic activation of the heart. If the synchronicity map is based on synchronization of a plurality of nodes, e.g. simultaneously, the determined node can be a node best suited for artificial stimulation, e.g. an optimum pacemaker electrode location, in addition to stimulation at the other nodes of the plurality of nodes, e.g. a plurality of pacemaker electrode locations.

Optionally, the method includes determining a desired location for one or more pacemaker electrodes on the basis of the heart synchronicity map. The optimal location for one or more pacemaker electrodes can e.g. be determined as described above. Pacemaker electrodes are sometimes positioned in cardiac blood vessels, such as cardiac veins. Therefore, optionally, the locations of such cardiac blood vessels are determined from the three dimensional model of the heart. Hence, the locations of the cardiac blood vessels can be included as nodes of the mesh of the three-dimensional model of the heart. Thus, stimulation of the heart at locations of the cardiac blood vessels, and the effect thereof on synchronicity can be determined and incorporated in the synchronicity maps.

Determining a desired location for a pacemaker electrode may include determining the node having the highest synchronicity. It is also possible that the method includes in a first step determining the node having the highest synchronicity within the group of nodes associated with cardiac veins. This note is then the candidate desired location for the pacemaker electrode. It will be appreciated that this node of the candidate location need not be the node with the highest synchronicity when looking at all nodes. In a second step it can be determined whether the synchronicity associated with the node of the candidate location is within a predetermined acceptable interval. If the synchronicity is outside the predetermined acceptable interval, in a third step a candidate location having highest synchronicity may be selected from the nodes not associated with cardiac veins. Thus, then pacing by epicardial wire or leadless pacing is proposed. It will be appreciated that in the computer implemented method these steps may be performed automatically. Hence, a desired location for a pacemaker electrode may be proposed to a clinician. It will be appreciated that the same steps can also be applied when determining desired locations for a plurality of pacemaker electrodes.

Thus, determining a desired location for a pacemaker electrode may include optimizing pacemaker electrode location in view of synchronicity as described above. Determining a desired location for a pacemaker electrode may also include taking into account the atrioventricular delay (AV delay) resulting from stimulation at a node. AV delay (delay between atria and ventricles) can be used to promote intrinsic AV conduction to the His Purkinje system, if that part is still intact. The synchronicity map may reflect the AV delay as the measure for heart activation synchronicity. Determining a desired location for a pacemaker electrode may also include taking into account the interventricular delay (VV delay), the delay between the 2 (3, 4, . . . ) stimuli sites in the ventricles. The synchronicity map may reflect the VV delay as the measure for heart activation synchronicity.

Once desired location(s) for one or more pacemaker electrodes have been determined, one or more actual pacemaker electrodes may be placed at the actual heart. The actual placing of the electrodes at the heart may be performed outside the scope of the present method. The one or more pacemaker electrodes may be placed at the desired locations. It will be appreciated that in practice the actual location of the one or more actual pacemaker electrodes at the actual heart may deviate from the determined desired location(s).

Optionally, the method includes obtaining location information of one or more actual pacemaker electrodes at the heart. The location information of the one or more actual pacemaker electrodes at the heart can obtained from the patient-specific three-dimensional anatomical model. The location information can e.g. be obtained by medical imaging, such as CT, and/or MRI. The location information of the one or more actual pacemaker electrodes at the heart can also be obtained from the three-dimensional model of electrical activation of the heart.

Optionally, the method includes indicating the location of the one or more actual pacemaker electrodes in the synchronicity map. Hence, a deviation between the determined desired location for the one or more pacemaker electrodes and the actual location of the one or more actual pacemaker electrodes can be assessed. Hence, for example a physical distance between the desired location and the actual location can be determined. Also, a difference between synchronicity resulting from stimulation at the desired location and synchronicity resulting from stimulation at the actual location can be determined. Hence, it can be assessed whether the difference between the desired pacemaker electrode location and the actual pacemaker electrode location warrants repositioning of the actual electrode and/or modifying pacemaker settings, such as not activating one or more of the actual pacemaker electrodes.

Optionally, the one or more actual pacemaker electrode locations can be used as the common stimulation site(s) as described above. Possibly an intrinsic activation site of the heart can be used as further common stimulation site. Hence, an actualized synchronicity map of the heart can be determined resulting from activation at the one or more actual pacemaker electrodes (and optionally intrinsic activation). From this actualized synchronicity map it may be determined whether the one or more actual pacemaker electrode locations are acceptable.

Optionally, when more than one actual pacemaker electrodes are placed at the heart, the method includes determining one or more actualized synchronicity maps, each actualized synchronicity map being determined by inclusion of the actual pacemaker electrode locations as common activation site, for all but one actual pacemaker electrode. Hence it can be determined repositioning of which one of the actual pacemaker electrodes has the most beneficial effect on total heart synchronicity. However, it can also be determined whether stimulation of one of the actual pacemaker electrodes does not (or hardly) contribute to, or even diminishes, total heart synchronicity. In such event, the pacemaker may be set not to activate that actual pacemaker electrode. Hence, heart synchronicity is not, or hardly, adversely affected by not activating that electrode, and power usage of the pacemaker can be diminished.

Similarly, it can be assessed whether repositioning or non-activation of further actual pacemaker electrodes would be of benefit.

In an embodiment, the invention relates to a computer implemented method for providing a representation of synchronicity of electrical activation of heart tissue. This method includes obtaining a patient-specific three-dimensional representation of the heart, lungs and thorax. The three-dimensional model includes a mesh representing an outer surface of the heart, e.g. the myocardial surface, e.g. including the septal wall, the mesh having a plurality of nodes. The mesh may include nodes associated with cardiac blood vessels, such as cardiac veins. This method includes obtaining ECG data while recording the exact locations the recording leads on the thorax. This method includes incorporating scar tissue in the three-dimensional representation. This method includes using an inverse calculation procedure to determine a three-dimensional intrinsic electrical activation model of the heart, including a mesh representing an outer surface of the heart, e.g. the myocardial surface optionally including the septum, the mesh having a plurality of nodes, each node having associated therewith a value of a time delay between stimulation of the heart and activation of the heart at that node. This method includes, for each node of the three-dimensional electrical activation model of the heart, defining a stimulus site at the location of that node in the three-dimensional anatomical model of the heart and determining synchronicity of the heart as a result of stimulation at the stimulus site.

The invention also relate to a computer implemented method for virtual pacemaker electrode implantation. The method includes obtaining a three-dimensional model of electrical activation of the heart. The method may include obtaining a three-dimensional patient-specific model of electrical activation of the heart of a specific patient. The three-dimensional model includes a mesh representing an outer surface of the heart, e.g. the myocardial surface optionally including the septal wall. The mesh has a plurality of nodes, each node having associated therewith a value representative of a time delay between stimulation of the heart at a stimulation site and activation of the heart at that respective node. The method includes virtually implanting a pacemaker electrode at a node of the three-dimensional model of the heart. The method includes on the basis of the three-dimensional model of electrical activation of the heart and a stimulus by the pacemaker electrode determining a modified three-dimensional model of electrical activation of the heart. Hence, electrical activation of the heart resulting from stimulation by the pacemaker electrode can be simulated. This provides the advantage that the effect of stimulation by the pacemaker electrode can be assessed prior to installing the pacemaker electrode in vivo, e.g. prior to surgery. Optionally, the method includes repeating the steps of virtually implanting a pacemaker electrode at a node of the three-dimensional model of the heart and on the basis of the three-dimensional model of electrical activation of the heart and a stimulus by that pacemaker electrode determining a modified three-dimensional model of electrical activation of the heart for a plurality of nodes. The method can then include selecting a preferred pacemaker electrode implantation site on the basis of a comparison of the obtained modified three-dimensional models of electrical activation of the heart. Thus, pacemaker electrode positioning can be optimized in view of synchronicity of the heart. Optionally, virtually implanting a pacemaker electrode at a node of the three-dimensional model of the heart and on the basis of the three-dimensional model of electrical activation of the heart and a stimulus by that pacemaker electrode determining a modified three-dimensional model of electrical activation of the heart for a plurality of nodes is performed for each node. In that case a synchronicity map can be produced and, if desired, used for selecting a preferred pacemaker electrode implantation site. Optionally, the method includes virtually implanting a plurality of pacemaker electrodes at respective nodes of the three-dimensional model of the heart and on the basis of the three-dimensional model of electrical activation of the heart and, e.g. simultaneous, stimuli by the plurality of pacemaker electrodes determining a modified three-dimensional model of electrical activation of the heart. Hence, the effect of stimulation by the plurality of pacemaker electrodes can be assessed prior to installing the pacemaker electrodes in vivo. It will be appreciated that it is possible that intrinsic activation of the heart is taken into account as described above.

Optionally, the method including obtaining location information of one or more actual pacemaker electrodes at the heart. Optionally, the method includes indicating the location of the one or more actual pacemaker electrodes in the three-dimensional model of electrical activation of the heart.

The invention also relates to a computer implemented method for providing a representation of electrical activation of heart tissue. The method includes obtaining a three-dimensional model of electrical activation of the heart. The method may include obtaining a three-dimensional patient-specific model of electrical activation of the heart of a specific patient. The three-dimensional model includes a mesh representing an outer surface of the heart, e.g. a surface of the myocardium e.g. with septal wall. The mesh has a plurality of nodes, each node having associated therewith a value representative of a time delay between stimulation of the heart at a stimulation site and activation of the heart at that respective node. The method includes defining in the model a stimulus site at a node of the three-dimensional model of the heart. The method includes on the basis of the three-dimensional model of electrical activation of the heart and stimulation at the stimulus site determining a modified three-dimensional model of electrical activation of the heart.

The invention also relates to a system for providing a representation of synchronicity of electrical activation of heart tissue. The system includes a processing unit. The processing unit is arranged for obtaining a three-dimensional model of electrical activation of the heart, such as a three-dimensional patient-specific model of electrical activation of the heart of a specific patient. The three-dimensional model includes a mesh representing an outer surface of the heart, such as the myocardial surface, e.g. with septal wall. The mesh has a plurality of nodes, each node having associated therewith a value representative of a time delay between stimulation of the heart at a stimulation site and activation of the heart at that respective node. The processing unit is arranged for each node of the three-dimensional model of the heart 1) defining a stimulus site at the location of that node in the three-dimensional model of the heart, 2) on the basis of the three-dimensional model of electrical activation of the heart determining a modified three-dimensional model of electrical activation of the heart resulting from stimulation at that node, and 3) determining a measure for heart activation synchronicity for the heart based on stimulation at that node. The processing unit is arranged for determining a heart synchronicity map representing a three-dimensional model of the heart, indicating at each node the respective measure for heart activation synchronicity. It will be appreciated that the synchronicity map may be displayed, e.g. on a screen. Controls may be provided for positioning, e.g. rotating and/or zoomin the synchronicity map on the screen.

The invention also relates to a non-transitory computer readable medium storing computer implementable instructions or a computer program product including computer program code portions which when implemented by a programmable computer cause the computer to:

obtain a three-dimensional model of electrical activation of the heart, the three-dimensional model including a mesh representing a surface of the myocardium, the mesh having a plurality of nodes, each node having associated therewith a value representative of a time delay between stimulation of the heart at a stimulation site and activation of the heart at that respective node;

for each node of the three-dimensional model of the heart:
define a stimulus site at the location of that node in the three-dimensional model of the heart;
on the basis of the three-dimensional model of electrical activation of the heart determine a modified three-dimensional model of electrical activation of the heart resulting from stimulation at that node;
determine a measure for heart activation synchronicity for the heart based on stimulation at that node; and
determine a heart synchronicity map representing a three-dimensional model of the heart, indicating at each node the respective measure for heart activation synchronicity.

It will be appreciated that any of the aspects, features and options described in view of the methods apply equally to system and computer program product and vice versa. It will also be clear that any one or more of the above aspects, features and options can be combined.

BRIEF DESCRIPTION OF THE DRAWINGS

The patent or application file contains at least one drawing executed in color. Copies of this patent or patent application publication with color drawing(s) will be provided by the Office upon request and payment of the necessary fee. Embodiments of the present invention will now be described in detail with reference to the accompanying drawings in which.

DETAILED DESCRIPTION

Figure 1:
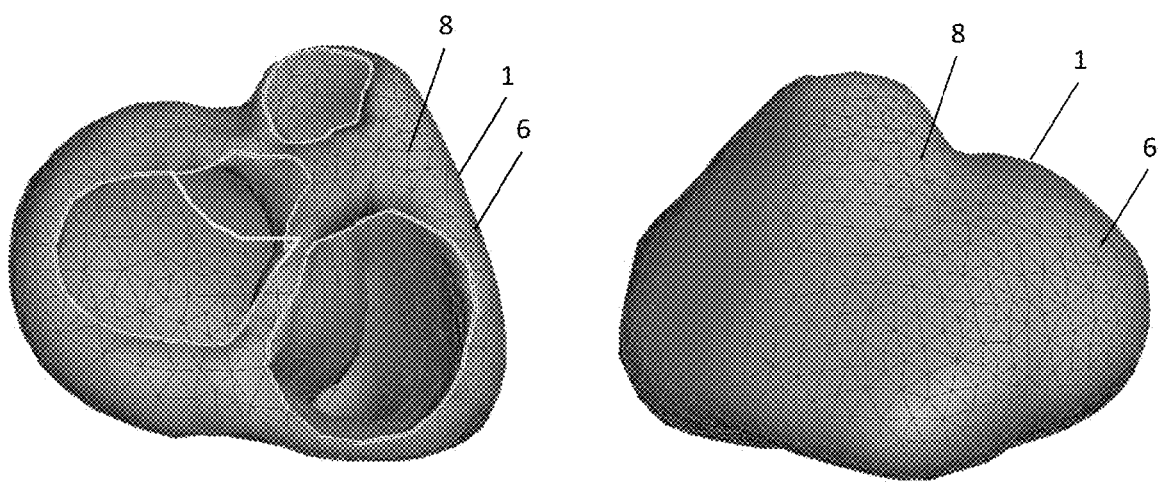
FIG. 1 is an example of a three-dimensional model of a heart.

FIG. 1 shows an example of a three dimensional model of a heart 1 seen in two different directions. The three dimensional (3D) model includes a mesh 6 representing an outer surface of the heart, here the myocardial surface. In this example the 3D model also includes the septal wall. The mesh 6 has a plurality of nodes 8. In this example, the mesh is a triangular mesh, wherein the surface of the heart is approximated by adjoining triangles.

Figure 2A:
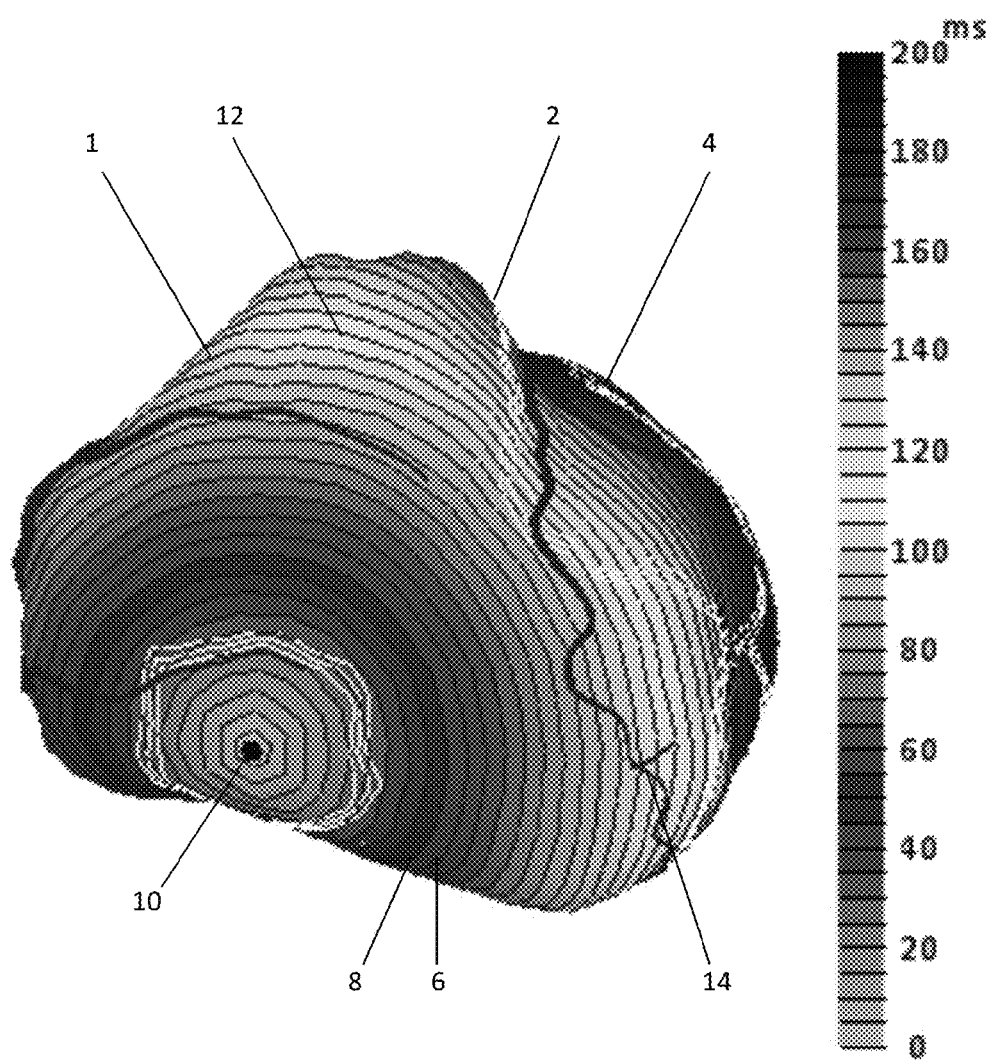
FIG. 2a is a schematic representation of a plan view of a 3D model of electrical activation of a heart.

FIG. 2a shows initial activation of a heart from a single stimulation location. The heart 1 represented in FIG. 2a is a model of electrical activation of a heart. FIG. 2a shows a representation of a ventricular surface of the myocardium with septal wall 2. FIG. 2a is a plane view of a three dimensional model 4 of electrical activation of the heart 1. In general the three dimensional model 4 includes a mesh 6 representing a ventricular surface of the heart, here an outer surface of the ventricular myocardium with septal wall, e.g. as represented in FIG. 1. The mesh 6 has a plurality of nodes 8. The heart 1 is electrically stimulated at a stimulation location 10. Upon electrical stimulation at the stimulation location 10, the electrical signals will travel through the heart tissue. Hence, different parts of the heart will be activated at different times. Each location on the heart has a particular delay relative to the initial stimulation. Each node 8 has associated therewith a value representative of a time delay between stimulation of the heart 1 at the stimulation location 10 and activation of the heart at that respective node 8. Locations that share the same delay time are connected by isochrones 12 in FIG. 2a. Herein, isochrones are defined as lines drawn on a 3D heart surface model connecting points on this model at which the activation occurs or arrives at the same time. The delay time for nodes across the heart surface is in this example also displayed by differing rendering colors. The vertical bar indicates the time delay in milliseconds associated with the respective colors. It will be appreciated that the stimulation location 10 can be the location of intrinsic activation of the heart 1.

Figure 3:
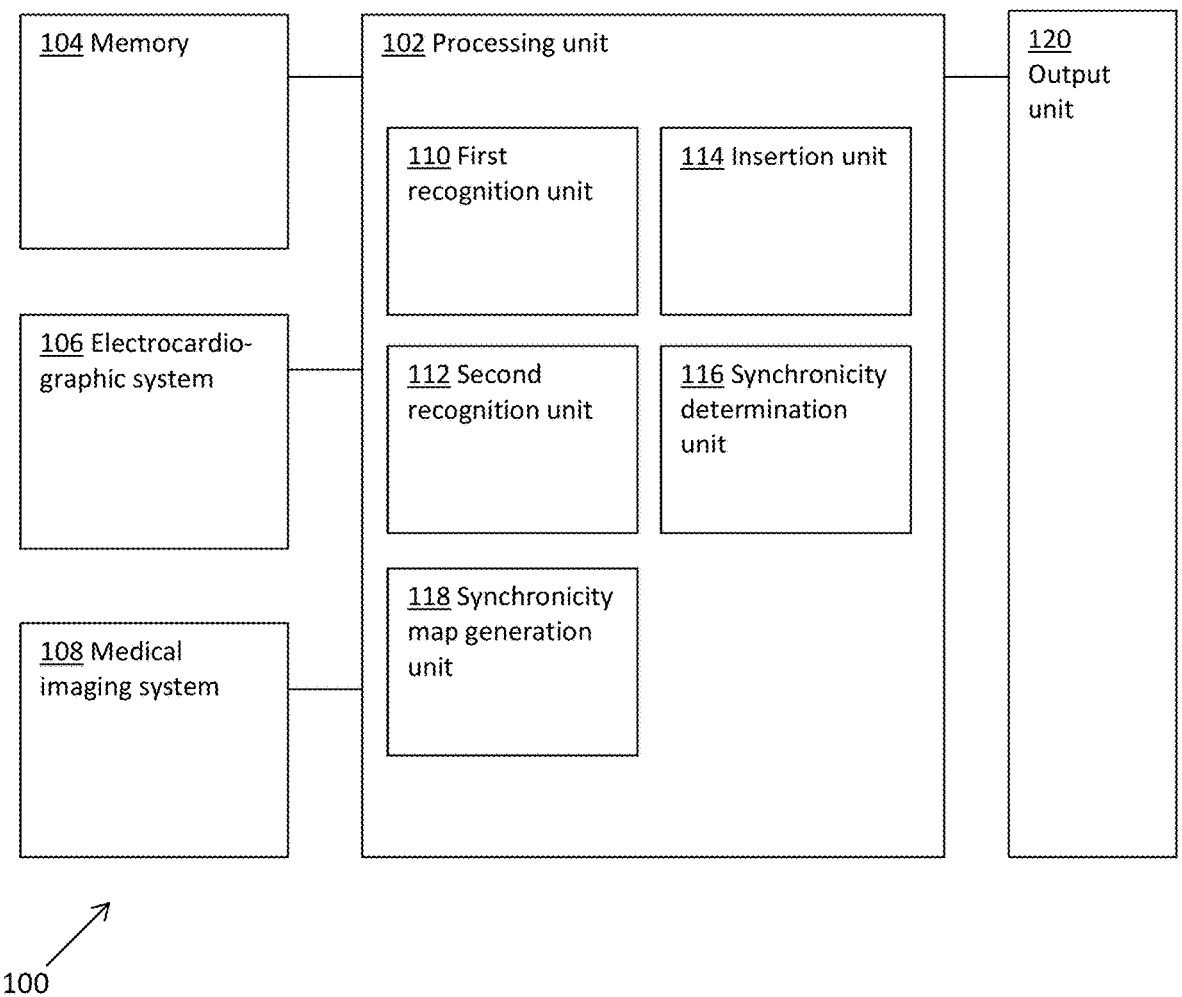
FIG. 3 is a schematic representation of a system.

FIG. 3 shows a schematic representation of a system 100 for providing a representation of synchronicity of electrical activation of heart tissue. The system includes a processing unit 102. The system in FIG. 3 further includes a memory 104.

The three dimensional model 4 of electrical activation of the heart 1 can be obtained from combined electrocardiographic and medical imaging data. This data is stored in the memory 104. The processing unit 102 can be communicatively connected to an electrocardiographic system 106 and a medical imaging system 108 for retrieving the data and storing it in the memory 104. A (e.g. non-invasive) electrocardiographic imaging (ECGI) method able to determine the cardiac activation from a, e.g. 12 lead, ECG can be applied by the processing unit 102 for determining the three dimensional model 4 of electrical activation of the heart. The ECG signals can be combined with a patient-specific three-dimensional anatomical model of the heart, lungs and torso in order to compute the positions of the cardiac isochrones. Hence, the patient-specific three dimensional model of electrical activation of the heart is provided. The patient-specific 3D anatomical model can be obtained from a magnetic resonance image (MRI) or computed Tomography (CT) images. Alternatively, or additionally, a 3D anatomical model showing closest conformity to the patient can be selected, and optionally modified, from a database including a plurality of 3D anatomical models. The selected, and optionally modified, 3D anatomical model can serve as the patient-specific 3D anatomical model.

The three dimensional model 4 of electrical activation of the heart 1 can also include further information. In the example of FIG. 2a the model 4 includes information on cardiac blood vessels, in particular cardiac veins. From the patient-specific three-dimensional anatomical model of the heart information can be obtained on the position of blood vessels on the myocardium. This information is added to the 3D model 4 of electrical activation in that nodes are indicated as being associated with such blood vessel. The blood vessel 14 is then identified and optionally visible in the model 4 of electrical activation of the heart 1. Optionally the processing unit 102 includes a first recognition unit 110 arranged for automatically retrieving information representative of the location of such blood vessels from the patient's three-dimensional anatomical model of the heart. The processing unit 102 may then automatically insert this information into the 3D model 4 of electrical activation of the heart 1.

The model 4 can also include information on scar tissue. Information on locations of scar tissue may be obtained from Delayed Enhancement MRI images and combined with the patients 3D anatomical model of the heart. Scar tissue can be simulated in the three-dimensional model 4 of electrical activation by reducing the propagation velocity. Scar tissue can also be accounted for by setting the transition from one node to another to very slow or non-transitional for the areas in the heart wall where scar tissue is present. Optionally the processing unit 102 includes a second recognition unit 112 arranged for automatically retrieving information representative of the location of such scar tissue from the patient-specific three-dimensional anatomical model of the heart. The processing unit 102 may then automatically insert this information into the 3D model 4 of electrical activation of the heart 1.

The thus obtained three-dimensional model 4 of electrical activation of the heart 1 can, according to an aspect of the invention, be used for obtaining further information on electrical activation of the heart.

In the three-dimensional model 4 of electrical activation of the heart 1 the time delay of activation from one node to another can be determined. This can be used to advantage to generate, on the basis of the 3D model 4 of electrical activation of the heart 1, other views resulting from initial stimulation at other nodes of the mesh 6. Thereto, the processing unit 102 includes an insertion unit 114. The insertion unit 114 takes the 3D model 4 of electrical activation of the heart 1 and defines a certain node as stimulation location. It will be appreciated that the 3D model 4 of electrical activation of the heart 1 assumes stimulation at a predetermined node. The insertion unit 114 may remove stimulation at that predetermined node for calculation purposes.

Figure 2B:
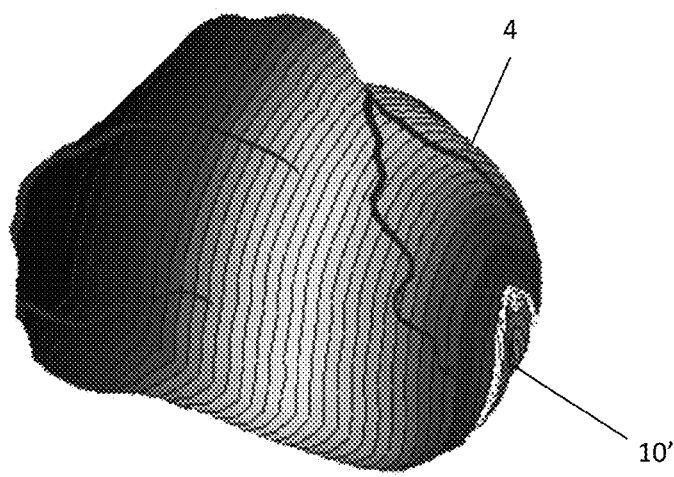
FIG. 2b is a schematic representation of a plan view of a 3D model of electrical activation of a heart.

FIG. 2b shows an example resulting from initial stimulation at another stimulation location 10', here an other node 8. It will be appreciated that a view resulting from initial stimulation at other nodes of the mesh 6 can be generated for each node of the mesh 6.

A particular electrical activation sequence of the entire heart 1, resulting from stimulation at a particular node, is summarized in a single parameter: heart activation synchronicity. The heart activation synchronicity provides an indication of how synchronous the entire heart is activated. For common situations a more synchronous activation of the heart is considered beneficial. The measure for heart activation synchronicity in this example is standard deviation (std) of the depolarization (dep) times of the heart. Hence, the heart activation synchronicity provides an indication of synchronicity of activation of the entire heart as a result of stimulation at the respective node. The processing unit 102 includes a synchronicity determination unit 116 arranged for determining the heart activation synchronicity.

According to an aspect of the invention, the heart activation synchronicity is determined separately for stimulation at each node. Hence, is provided a measure of heart activation synchronicity for each node of the mesh. The processing unit 102 includes a synchronicity map generation unit 118 arranged for generating a synchronicity map based on the calculation of the heart activation synchronicity for each node by the synchronicity determination unit 116. The processing unit 102 is communicatively connectable with an output unit 120 arranged for outputting the synchronicity map 15 and/or alternative data to a user. The output unit may be a display unit, a printer, a messaging unit or the like.

Figure 2C:
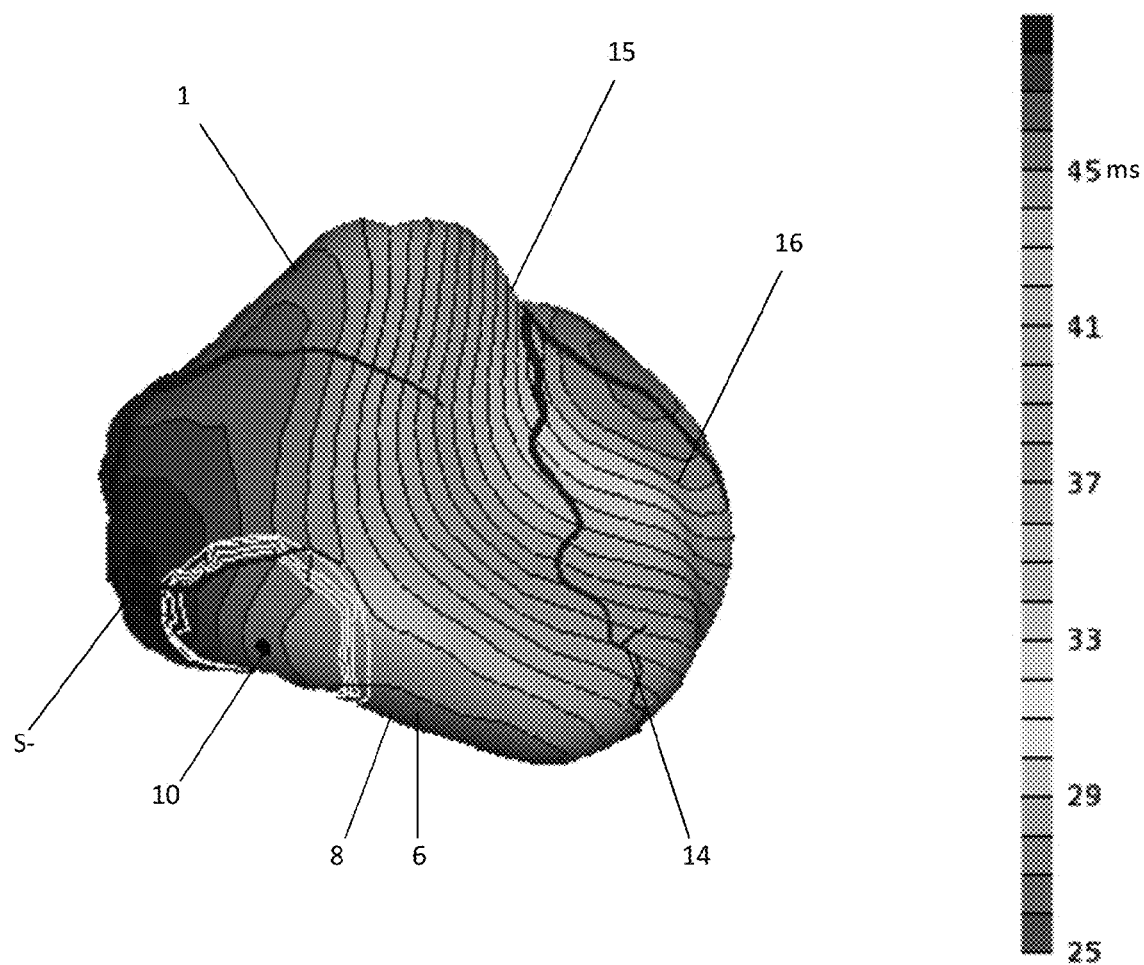
FIG. 2c is a schematic representation of a plan view of a synchronicity map.
Figure 2D:
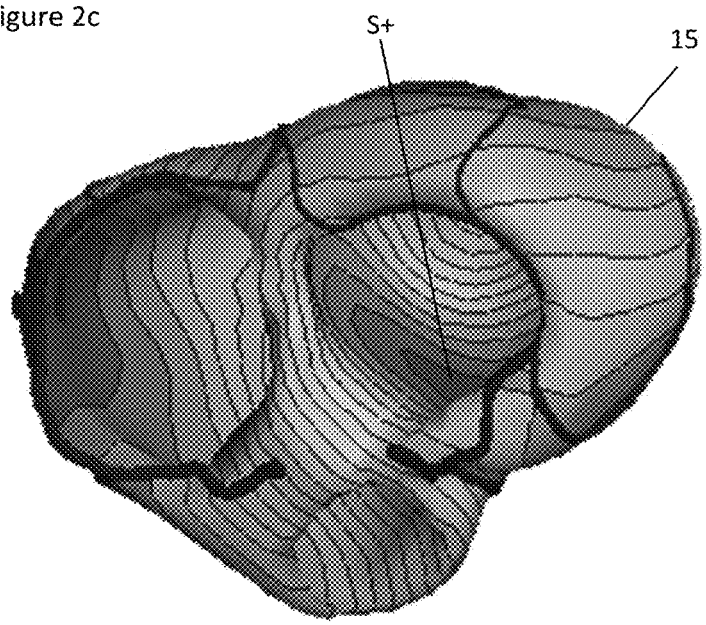
FIG. 2d is a schematic representation of a plan view of a synchronicity map.

FIG. 2c shows an example of a heart synchronicity map 15. In this FIG. 2c at each node the respective measure for heart activation synchronicity is indicated. In this example the indication is in false colors. In FIG. 2c iso-sync-lines 16 are indicated. These iso-sync-lines connect nodes having a same measure of heart activation synchronicity. The heart synchronicity map provides an easy singular three-dimensional overview showing which locations on the heart result in good heart activation synchronicity and which locations on the heart result in poor heart activation synchronicity, if the heart were stimulated at such locations. It can for instance be seen that in this example the original stimulation location 10 does not provide particularly good synchronization with a heart activation synchronicity value of approximately 45 ms standard deviation of the depolarization times of the heart. In this example the least favorable stimulation location, here the location with the highest heart activation synchronicity value, is indicated at S−. In this example the most favorable stimulation location, here the location with the lowest heart activation synchronicity value, is indicated at S+. It is noted that the most favorable stimulation location S+ can best seen when looking at the synchronicity map 15 from another direction, as shown in FIG. 2d.

An other example of a measures for heart activation synchronicity is a range in depolarization times (maximum depolarization time—minimum depolarization time). The range in depolarization times may be corrected for cycle length. An other example of a measures for heart activation synchronicity is a standard deviation of the Left Ventricle (LV) depolarization times only. An other example of a measures for heart activation synchronicity is a delay between stimulus and Septum activation. An other example of a measures for heart activation synchronicity is a AV delay. An other example of a measures for heart activation synchronicity is a VV delay. It will be appreciated that the measure for heart activation synchronicity can be chosen in dependence of the task at hand and/or in dependence of a specific condition or abnormality experienced in the patient.

Figure 4A:
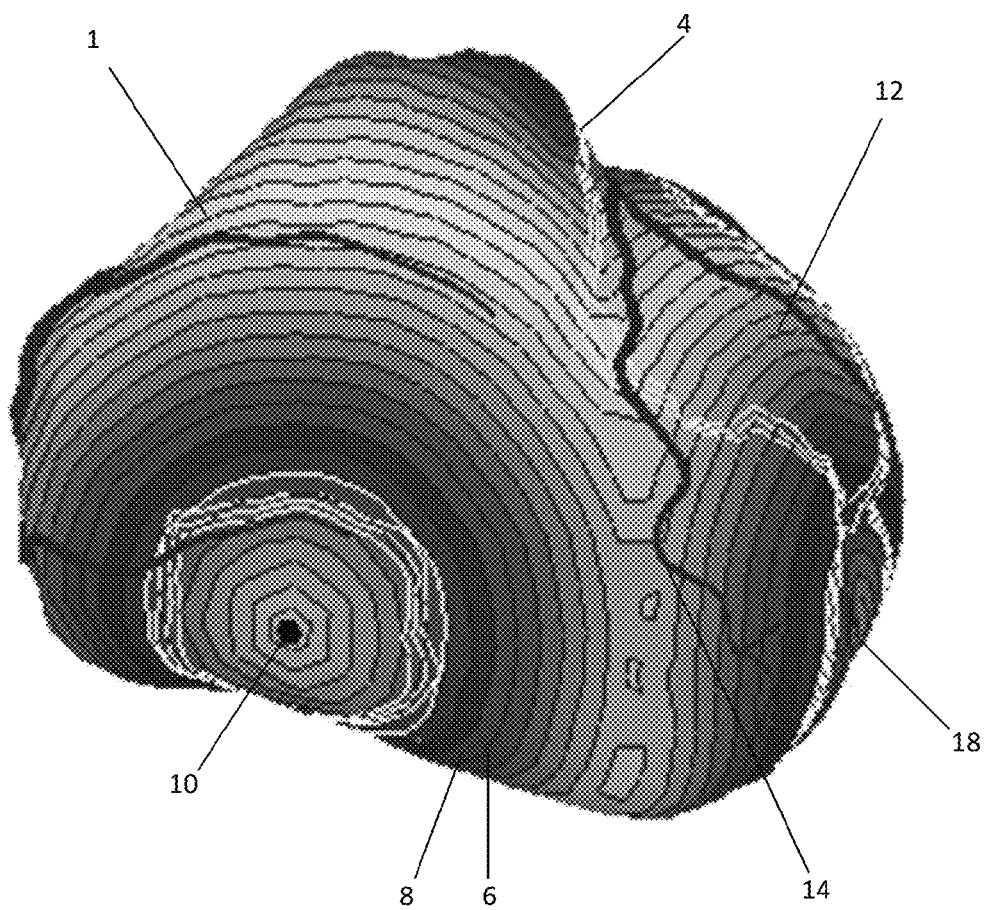
FIG. 4a is a schematic representation of a plan view of a 3D model of electrical activation of a heart.

In FIG. 4a a second example is shown. In this example a second stimulation location 18 is defined. Then electrical activation of the heart 1 is calculated using the three-dimensional model 4 of electrical activation of the heart 1 and simultaneous stimulation at the first stimulation location 10 and the second stimulation location 18. It will be appreciated that in this example the insertion unit 114 does not remove stimulation at the first location 8 for calculation purposes. FIG. 4a shows the calculated resulting electrical activation of the heart 1. It will be appreciated that the total activation time shortens due to the addition of the second stimulation location 18. In this example the first stimulation location 10 represents the location of intrinsic activation of the heart 1 or a first chosen location to stimulate or a stimulation generated by an already present pacemaker lead within the heart.

Figure 4B:
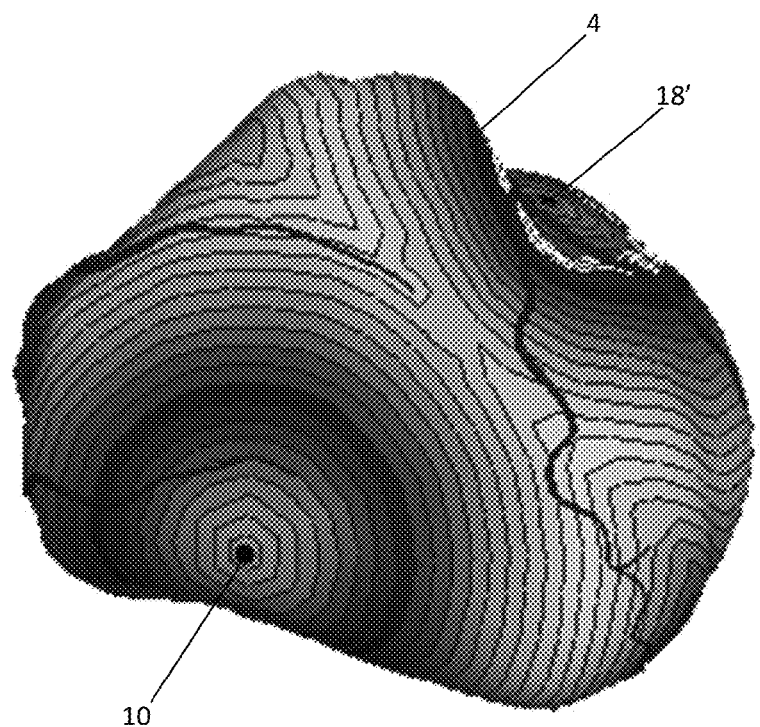
FIG. 4b is a schematic representation of a plan view of a 3D model of electrical activation of a heart.

FIG. 4b shows an example resulting from initial stimulation at other second stimulation location 18', respectively, simultaneous with stimulation at first stimulation location 10. It will be appreciated that a view resulting from initial stimulation at other second nodes of the mesh 6, simultaneous with stimulation at a first node associated with the first stimulation location 10, can be generated for each node of the mesh 6.

Figure 4C:
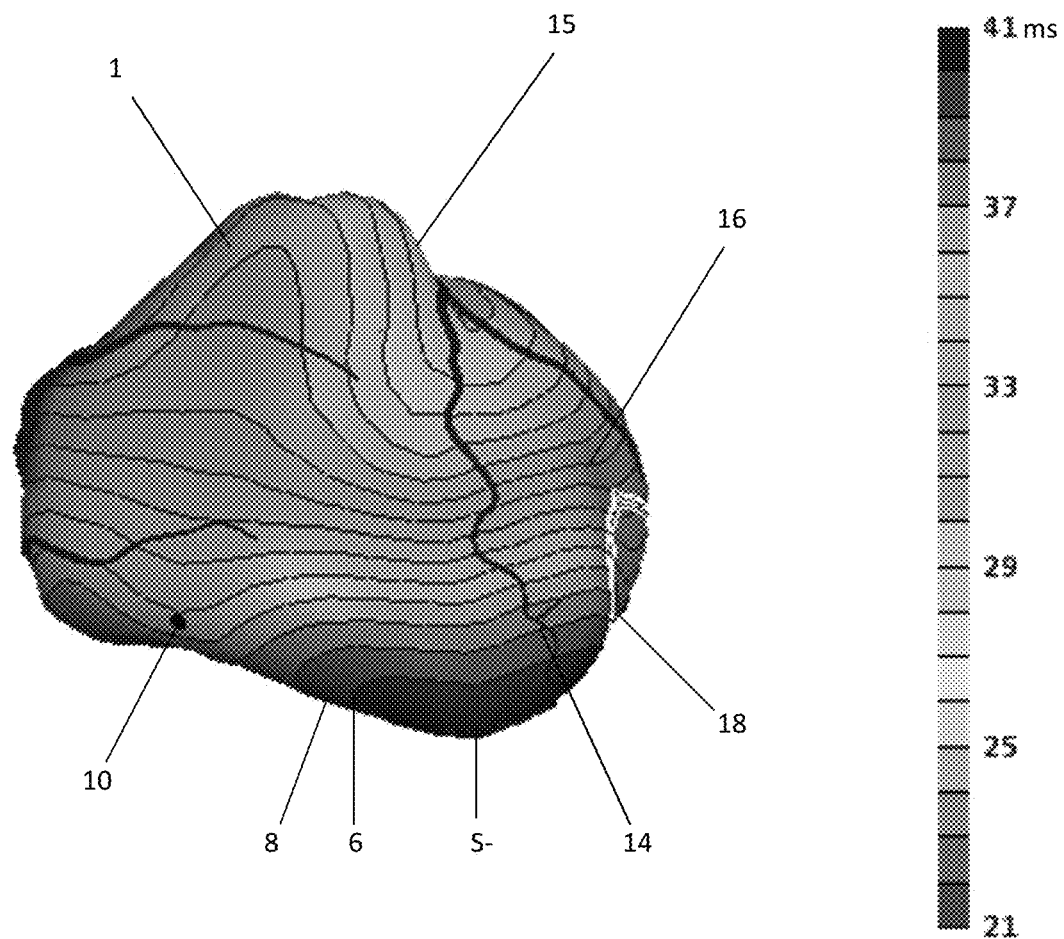
FIG. 4c is a schematic representation of a plan view of a synchronicity map.
Figure 4D:
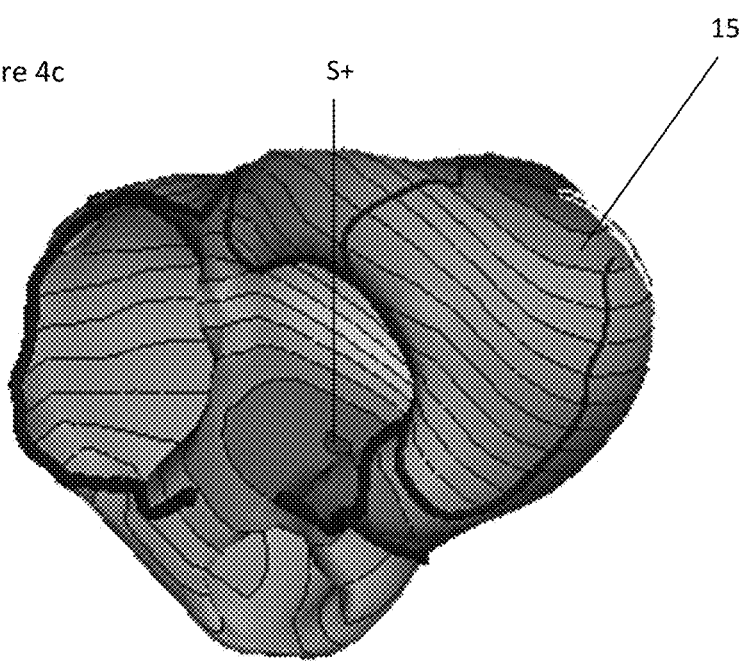
FIG. 4d is a schematic representation of a plan view of a synchronicity map.

In the example of FIGS. 4c and 4d a particular electrical activation sequence of the entire heart 1, resulting from stimulation at the second stimulation location 18 simultaneous with stimulation at the first stimulation location 10, is summarized as the heart activation synchronicity. The heart activation synchronicity then again provides an indication of how synchronous the entire heart is activated. According to an aspect of the invention, the heart activation synchronicity is determined separately for stimulation at each node simultaneous with stimulation at the first 10 and second 18 stimulation locations. Hence, is provided a measure of heart activation synchronicity for each node, acting as third stimulation location, of the mesh. FIG. 4c shows an example of a heart synchronicity map. The heart synchronicity map of FIG. 4c provides an easy singular three-dimensional overview showing which locations on the heart result in good heart activation synchronicity and which locations on the heart result in poor heart activation synchronicity, if the heart were stimulated at such locations simultaneous with stimulation at the first stimulation location 10 and the second stimulation location 18. In this example the least favorable third stimulation location, here the location with the highest heart activation synchronicity value of approximately 41 ms standard deviation of the depolarization times of the heart when stimulated simultaneously with the first stimulation location 10 and the second stimulation location 18, is indicated at S−. In this example the most favorable third stimulation location, here the location with the lowest heart activation synchronicity value when stimulated simultaneously with the first stimulation location 10 and the second stimulation location 18, is indicated at S+. It is noted that the most favorable stimulation location S+ can best seen when looking at the synchronicity map 15 from another direction, as shown in FIG. 4d.

Figure 5:
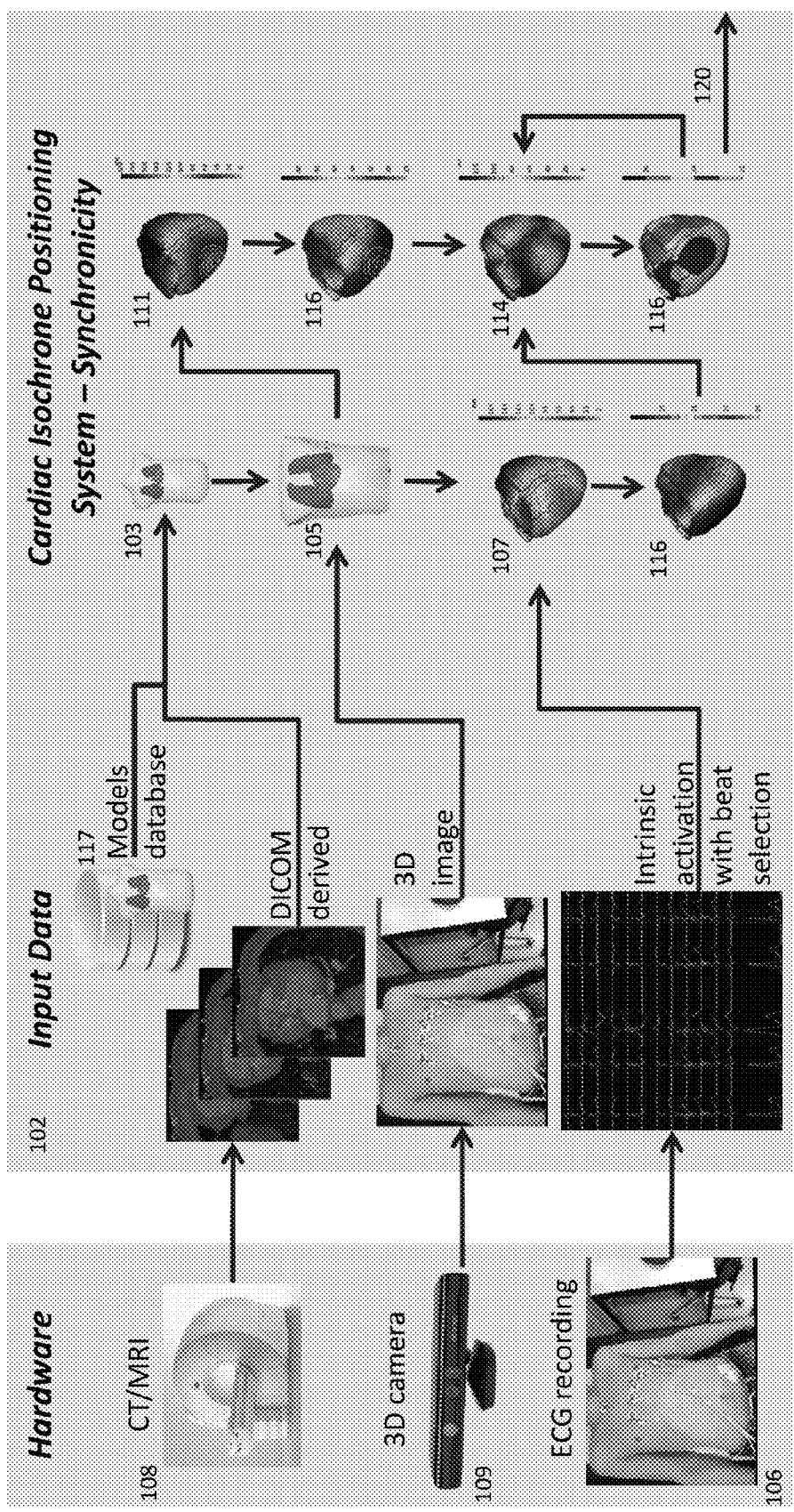
FIG. 5 is a schematic representation of a system.
Figure 6:
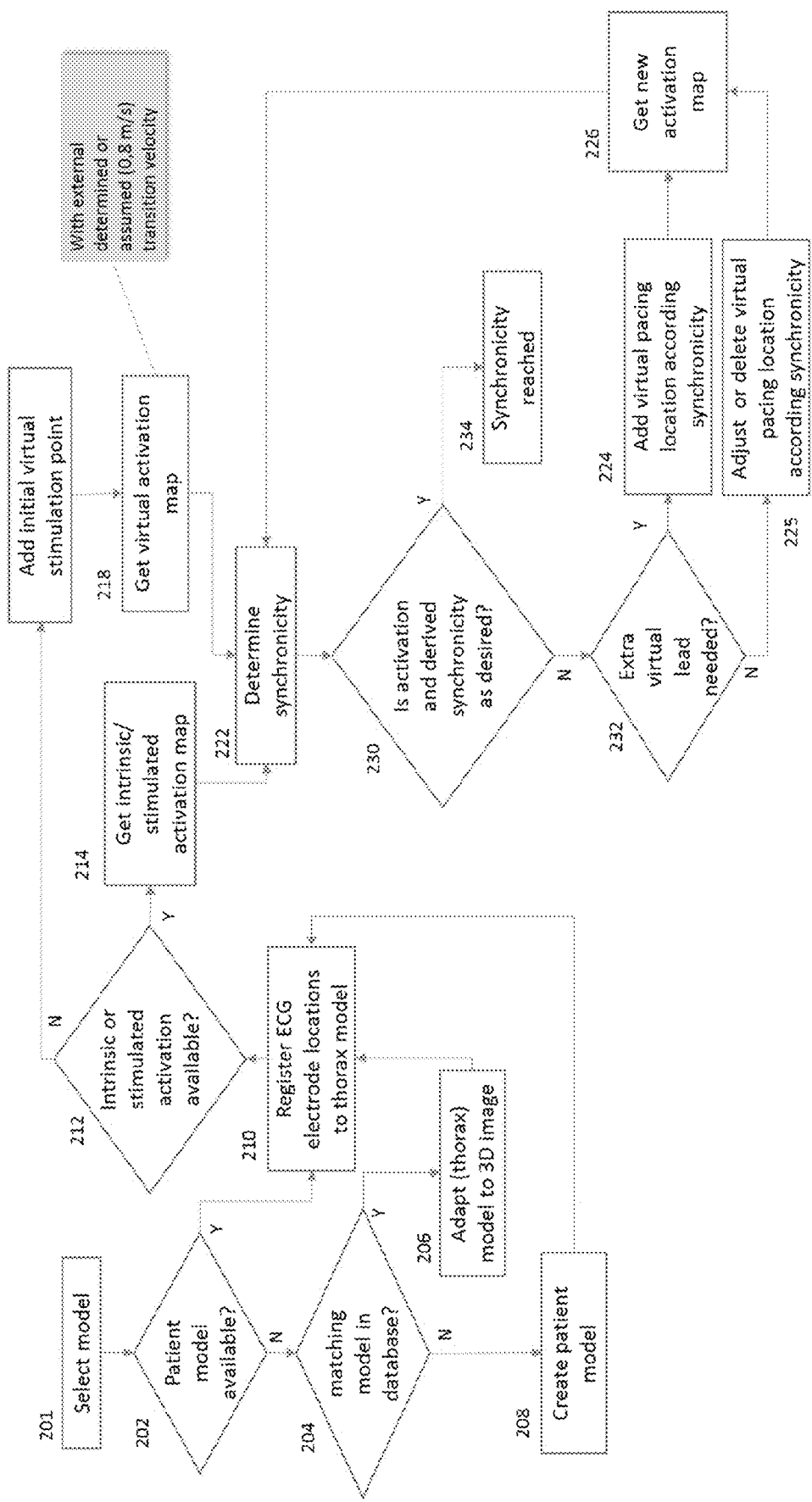
FIG. 6 is a schematic flow chart of a method.

FIG. 5 shows another schematic representation of a system 100 for providing a representation of synchronicity of electrical activation of heart tissue. FIG. 6 shows an exemplary schematic flow chart for a method of determining heart synchronicity.

The system includes a processing unit 102 which receives data from hardware modules. Optionally from an electrocardiographic system 106 the processing unit 102 receives ECG data. From a medical imaging system 108 the processing unit receives patient-specific anatomical data. Optionally, from a positioning system 109 the processing unit 102 receives information on the positions of ECG leads relative to the anatomy of the patient, e.g. a 3D image and the torso model mapped to the 3D image. ECG lead positions can also be entered into the system manually.

From the patient-specific anatomical data the processing unit 102 determines the synchronicity map 15. Thereto in this example the processing unit 102 includes the following units, and performs the following steps.

For generating the synchronicity map the processing unit 102 needs a patient-specific 3D anatomical model of the thorax of the patient and the size, orientation and location of the heart within the thorax. Such model needs to be selected 201 for further use by the processing unit. It can be that such model is already available 202. If the model is not yet available, in this example a retrieval unit 103 checks 204 whether a suitable anatomical model for this patient is present in a database 117. If so, the retrieval unit 103 retrieves that suitable anatomical model from the database 117. The retrieval unit may adapt the anatomical model from the database to the 3D image of the patient so as to transform 206 the selected anatomical model into a (quasi) patient-specific 3D anatomical model. If no suitable patient-specific anatomical model is available in the database 117, the retrieval unit 103 generates the patient-specific anatomical model on the basis of the received patient-specific anatomical 3D image data.

Optionally, the patient-specific 3D model also includes a size, orientation and/or location of other structures such as the lungs. The patient-specific 3D model can be a volume conductor model.

From the information on the positions of ECG leads and the patient-specific model, a lead locator module 105 can determine corresponding positions of the ECG leads in the patient-specific model to provide 210 an enhanced patient-specific model.

With the patient-specific anatomical model and/or the enhanced patient-specific model available, it is checked 212 whether ECG data representative of intrinsic or stimulated activation is available. If intrinsic activation data or pacing stimulation from one or more already present pacemaker leads is available, an activation unit 107 determines 214 a 3D electric model of current activation of the heart of the patient on the basis of the (enhanced) patient-specific model and the ECG data.

If no ECG data on intrinsic or stimulated activation is available, a virtual stimulation unit 111 adds 216 an initial virtual stimulation to an electrical model of the heart based on previously determined and/or assumed transition velocities between nodes. An assumed transition velocity may e.g. be 0.8 m/s. It will be appreciated that the electrical model may include arteries, veins and/or scar tissue as explained above. This yields 218 a 3D electric model of virtual activation of the heart of the patient.

From the 3D electric model of intrinsic, stimulated, or virtual activation of the heart of the patient a synchronicity determination unit 116 determines 222 a synchronicity map 15 as described above.

On the basis of the synchronicity map, the processing unit 102 can determine 230 whether the artificial stimulation location or virtual stimulation location resulted in optimum activation and synchronicity. If so, the process can provide 234 a calculation of preferred stimulation locations for a patient's heart.

If the optimum synchronicity has not been reached, it is determined 232 whether an extra virtual stimulation location according the synchronicity map should be added or if virtual stimulation location should be moved or changed with respect to the timing parameters.

If a virtual stimulation location should be moved or changed, the system will adjust 225 the artificial or virtual stimulation location accordingly. Then activation can be determined anew 226 and synchronicity can be recalculated 222 until activation is as desired 230.

The system can also virtually adapt the current artificial stimulation location, i.e. pacemaker lead, with respect to its current stimulation parameters to reach optimum synchronicity.

The system can also be used for assessing multiple stimulation. The multiple stimulation can e.g. be a combination of intrinsic activation and stimulated activation (pacing). The multiple stimulation can e.g. be a multiple stimulated activation (pacing). It is possible that the user or the processing unit 102 determines 232 whether an additional stimulation location, e.g. an additional pacemaker lead, would be desirable.

If an additional stimulation location is desired, an additional stimulation location is inserted by insertion unit 114. Then activation for the situation with the original stimulation location (intrinsic, stimulated or virtual) and the added virtual stimulation location can be determined anew 226 and synchronicity can be recalculated 222.

On the basis of the synchronicity map, the processing unit 102 can determine 230 whether the additional virtual stimulation location resulted in optimum synchronicity. If the optimum synchronicity has not been reached, it is determined 232 whether an extra virtual stimulation location according the synchronicity map should be added or if virtual stimulation location should be moved, changed with respect to the timing parameters or even removed. In such case the process is repeated (third, fourth, fifth, etc.).

Thus, based on the patient specific cardiac activation model a cardiac synchronicity model can be determined. The synchronicity model can be a 3D heart surface model including iso-sync-lines. In the synchronicity model, the iso-sync-lines represent synchronicity of activation of the heart. This synchronicity can be based on specific activation conditions, such as right ventricle activation at a lead position of a pacemaker.

As an example, the synchronicity model can be generated as follows.

The activation isochrones for the intrinsic (Left Bundle-Branch Block, LBBB) pattern are determined. This can be done in the following steps.

1a) A patient-specific anatomical 3D model of the heart, lungs and thorax is generated, e.g. on the basis of an MRI or CT image of the patient or derived from a model taken from a database adapted to the patients dimensions, e.g. with use of the 3D camera. The anatomical 3D model can e.g. include a 3D surface model of the heart, a 3D surface model of the lungs and a 3D surface model of the thorax. A 3D surface model can be a close approximation of the actual surface, by means of a mesh of a plurality of polygons, such as triangles, connected at their corners. The interconnected corners form nodes of the mesh.

1b) An ECG, e.g. a 12-lead ECG, is measured. The exact locations of the electrodes of the ECG device on the thorax may be recorded. The positions of the electrodes in the three dimensional anatomical model are used for estimating the distribution, fluctuation and/or movement of electrical activity through heart tissue. The exact locations of the recording leads of the ECG device may be entered in the anatomical 3D representation of the thorax.

1c) Optionally, scar tissue is incorporated in the anatomical 3D representation of the heart. The presence and location of scar tissue may be derived from Delayed Enhancement MRI images.

1d) The measurements per recording lead of the ECG device are related to the heart and torso geometry. Using an inverse procedure the intrinsic activation can be determined. The distribution, fluctuation and/or movement of electrical activity through heart tissue may e.g. be based upon a myocardial distance function, a fastest route algorithm, shortest path algorithm and/or fast marching algorithm.

2) Once the activation isochrones for the intrinsic (LBBB) pattern have been determined, a stimulus site is added to the intrinsic activation for each node on the heart and the desired synchronicity of the heart is computed from the outcome. Node here means, an intersection point of the triangles the anatomical 3D heart model is based on.

The above methods can also be used for determining an optimum location for placement of a cardiac pacemaker electrode. To determine an optimal pacing site synchronicity maps can be computed.

The intrinsic activation in combination with the found/chosen best stimulation location results in a new cardiac isochrone positioning map.

Figure 7A:
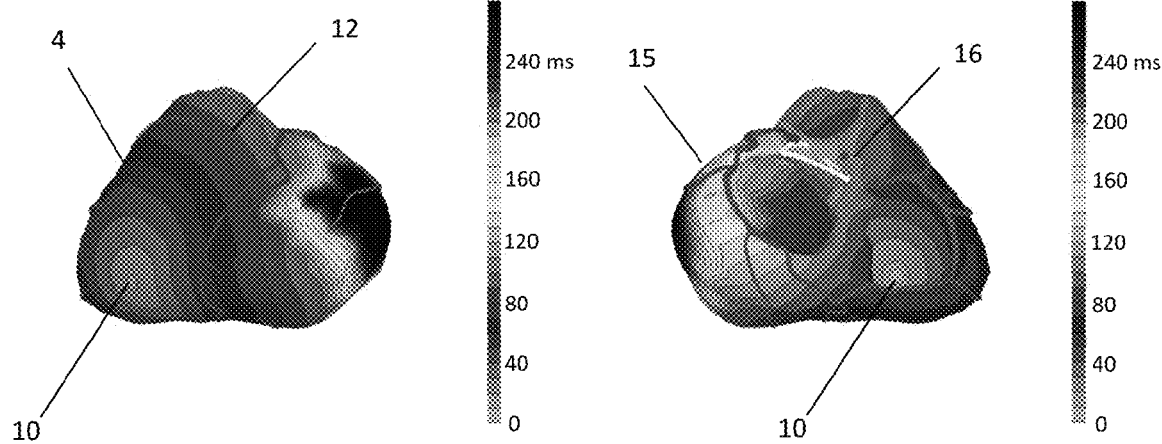
FIG. 7a is a schematic representation of a LAO and a PA view of a 3D model of electrical activation of a heart.
Figure 7B:
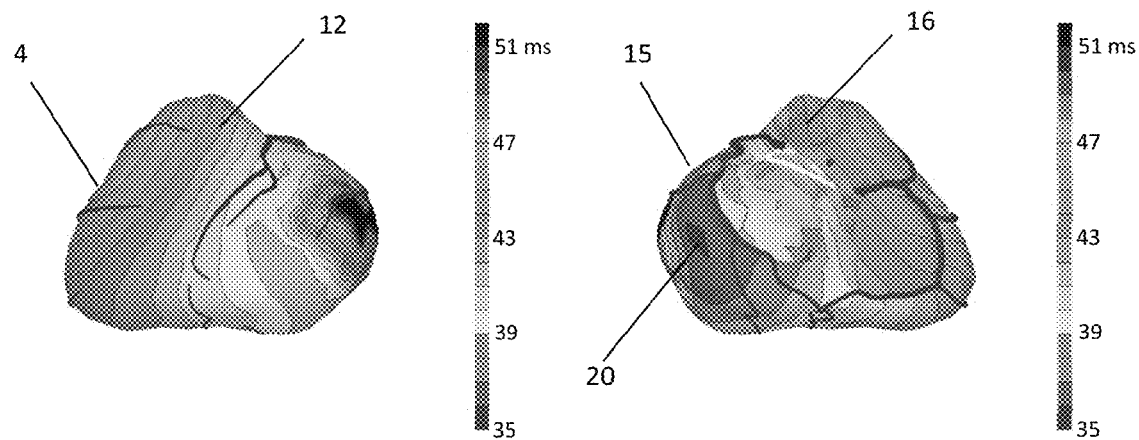
FIG. 7b is a schematic representation of a LAO and a PA view of a synchronicity map.

FIG. 7a shows an example of intrinsic activation of an LBBB pattern. On the left FIG. 7a shows the left anterior oblique (LAO) view, on the right the posteroanterior (PA) view of a three-dimensional model 4 of intrinsic electrical activation of one and the same heart 1. FIG. 7b shows an example of a synchronicity map 15 for the heart 1 shown in FIG. 7a. On the left FIG. 7b shows the LAO view, on the right the PA view. The synchronicity map of FIG. 7b shows the standard deviation of the depolarization times of the heart as a result of one extra stimulation location combined with the intrinsic activation of the heart. From FIG. 7b it can be seen that choosing the additional stimulation location in the area on the basal left free wall 20 reduces the standard deviation of the depolarization times of the heart the most. Therefore, in this example the area on the basal left free wall could be selected as best location for a pacemaker electrode, such as a CRT lead. It will be appreciated that an updated three-dimensional model of electrical activation of the heart can be generated including intrinsic activation simultaneous with stimulation in the area on the basal left free wall.

This map can then be used to generate a new synchronicity map to check the lead location(s) in the right chamber. By doing this:

It can be determined if that lead(s) must stimulate as well instead of only sensing, It can be determined if that lead(s) should be shifted, It can be determined if extra stimulation lead(s) should be added.

It can be determined whether intrinsic AV conduction is beneficial. Intrinsic AV conduction will generally conduct to the right bundle, after which the LV needs to be activated by stimulating the LV. All can also be reversed, i.e. with a RBBB wait for LV activation and stimulate the RV free wall at an optimal position By repeating the procedure for both left and right ventricle, the exact location and timing of cardiac pacing can be fine-tuned.

When the intrinsic activation signal is not usable due to severe damage of the heart, the whole procedure can be using only simulated (pacemaker) stimulation instead of the intrinsic activation. The procedure steps 1b and 1d can be omitted in that case. The whole procedure will then be based on artificial activation.

Figure 8A:
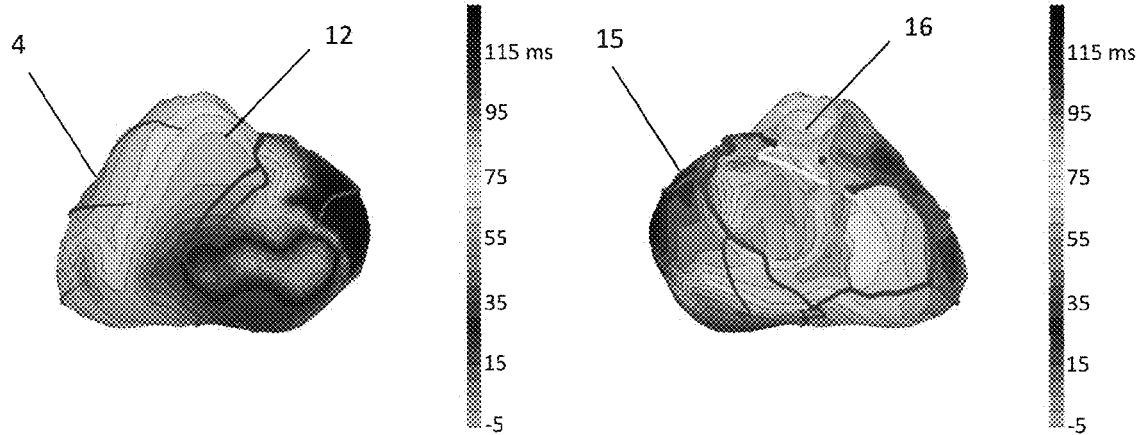
FIG. 8a is a schematic representation of a LAO and a PA view of a 3D model of electrical activation of a heart.
Figure 8B:
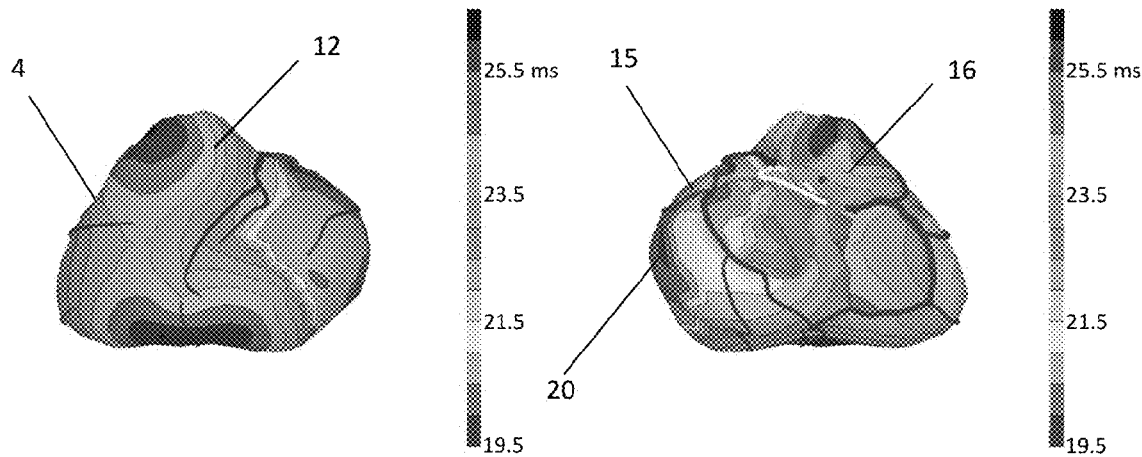
FIG. 8b is a schematic representation of a LAO and a PA view of a synchronicity map.

FIG. 8a shows an example of left stimulated activation of an LBBB pattern. On the left FIG. 8a shows the LAO view, on the right the PA view. FIG. 8b shows an example of a synchronicity map 15 for the heart 1 shown in FIG. 8a. On the left FIG. 8b shows the LAO view, on the right the PA view. The synchronicity map of FIG. 8b shows the standard deviation of the depolarization times of the heart as a result of one extra stimulation location combined with the left stimulated activation of the heart. From FIG. 8b it can be seen that choosing the additional stimulation location in the area on the basal left free wall 20 reduces the standard deviation of the depolarization times of the heart the most. Therefore, in this example the area on the basal left free wall could be selected as best location for a pacemaker electrode, such as a CRT lead. It will be appreciated that an updated three-dimensional model of electrical activation of the heart can be generated including intrinsic activation simultaneous with stimulation in the area on the basal left free wall.

The whole procedure could be determined also during the implantation procedure to find most optimal pacing sites.

Herein, the invention is described with reference to specific examples of embodiments of the invention. It will, however, be evident that various modifications and changes may be made therein, without departing from the essence of the invention. For the purpose of clarity and a concise description features are described herein as part of the same or separate embodiments, however, alternative embodiments having combinations of all or some of the features described in these separate embodiments are also envisaged.

When selecting the 3D anatomical model of the torso for a patient from the database, the database includes a plurality of mutually different 3D anatomical models. The 3D anatomical models can e.g. differ in dimensions of the torso and internal structures such as heart and lungs. The 3D anatomical models can represent reference torsos that correspond to different values for parameters such as one or more of gender, age, weight, body length, chest circumference, frame size, and body-mass-index. It will be appreciated that each 3D anatomical model in the database can e.g. be derived from a medical imaging modality, such as MRI, CT, PET-CT, ultrasound, or the like, from a respective reference subject. It is also possible that some or all 3D anatomical models in the database are fictitious renderings of fictitious reference patients.

Selecting the most appropriate 3D anatomical model from the database may be performed on the basis of the parameters, such as gender, age, weight, body length, chest circumference, frame size, BMI, etc. Such selection may be automated on the basis of parameters of the subject that are already known, e.g. from measurements, questions or tests. The selection may also be based on visual comparison of the 3D image of the torso of the subject with the 3D models in the database. Such selection may be automated on the basis of computer recognition of the shape of the 3D image of the torso and the shape of the torsos of the 3D anatomical models. It will be appreciated that the higher the number of different 3D models in the database, the better the match between one of the 3D models in the database and the torso of the patient. The 3D anatomical model selected from the database can, for the purpose of this invention, be used as the patient-specific 3D anatomical model.

Conformity between the torso of the patient and the selected 3D model may be further enhanced by scaling the selected 3D model to the 3D image of the torso of the subject, and/or scaling the 3D image to the 3D torso model. The 3D anatomical model can be scaled so as to have the outer surface of the torso in the model correspond with the outer surface of the torso of the subject as obtained from the 3D image. Such scaling may include skewing or warping of the 3D anatomical model. While the 3D anatomical model is scaled, also dimensions and positions of internal structures such as the lungs and heart can be scaled.

Conformity between the torso of the patient and the selected 3D model can be further enhanced by taking values of the parameters of the subject into account when scaling the 3D anatomical model. For example, the scaling can be dependent on the amount of body fat and frame size of the subject. In a subject with more body fat, the chest circumference can be larger in relation to the dimensions of heart and lungs, than in a subject with less body fat.

Conformity between the torso of the patient and the selected 3D model can be further enhanced by modifying a position of the heart in the selected 3D anatomical model on the basis of values of parameters of the subject. Such parameter can e.g. be weight or age of the subject. The weight can be indicative of a large belly, which pushes the heart upwards. Therefore, a vertical position of the heart in the 3D anatomical model can be modified on the basis of weight of the subject. The heart tends to be positioned more horizontally with increasing age. Therefore, a rotation of the heart in the 3D model can be modified on the basis of the age of the subject.

In the examples, the three-dimensional model includes a mesh representing a surface of the myocardium, the mesh having a plurality of nodes. It is also possible that the 3D model includes a volume mesh, e.g. including cubes or tetrahedrons.

It will be appreciated that the processing unit can be embodied as dedicated electronic circuits, possibly including software code portions. The processing unit can also be embodied as software code portions executed on, and e.g. stored in, a memory of, a programmable apparatus such as a computer.

Although the embodiments of the invention described with reference to the drawings comprise computer apparatus and processes performed in computer apparatus, the invention also extends to computer programs, particularly computer programs on or in a carrier, adapted for putting the invention into practice. The program may be in the form of source or object code or in any other form suitable for use in the implementation of the processes according to the invention. The carrier may be any entity or device capable of carrying the program.

For example, the carrier may comprise a storage medium, such as a ROM, for example a CD ROM or a semiconductor ROM, or a magnetic recording medium, for example a floppy disc or hard disk. Further, the carrier may be a transmissible carrier such as an electrical or optical signal which may be conveyed via electrical or optical cable or by radio or other means, e.g. via the internet or cloud.

When a program is embodied in a signal which may be conveyed directly by a cable or other device or means, the carrier may be constituted by such cable or other device or means. Alternatively, the carrier may be an integrated circuit in which the program is embedded, the integrated circuit being adapted for performing, or for use in the performance of, the relevant processes.

However, other modifications, variations, and alternatives are also possible. The specifications, drawings and examples are, accordingly, to be regarded in an illustrative sense rather than in a restrictive sense.

For the purpose of clarity and a concise description features are described herein as part of the same or separate embodiments, however, it will be appreciated that the scope of the invention may include embodiments having combinations of all or some of the features described. In the claims, any reference signs placed between parentheses shall not be construed as limiting the claim. The word 'comprising' does not exclude the presence of other features or steps than those listed in a claim. Furthermore, the words 'a' and 'an' shall not be construed as limited to 'only one', but instead are used to mean 'at least one', and do not exclude a plurality. The mere fact that certain measures are recited in mutually different claims does not indicate that a combination of these measures cannot be used to an advantage.

The invention claimed is:

1. A method for determining a patient-specific pacemaker electrode location for implantation of the pacemaker electrode at the patient's heart, including:

obtaining, by a computer, a patient-specific three-dimensional model of the heart of the patient, the three-dimensional model including a mesh representing a surface of the myocardium, the mesh having a plurality of nodes, each node of the plurality of nodes corresponding to a respective location on the patient's heart, each node of the plurality of nodes having associated therewith a model time delay value representative of a time delay of electrical activation of a location on the patient's heart corresponding to said node;

for each particular node of the three-dimensional model of the heart, by the computer:

a) defining the particular node as a reference node;

b) using the model time delay values of the nodes in the three-dimensional model of the heart, determining, for each respective node of the plurality of nodes, a relative time delay value representative of a time delay of electrical activation at the location on the patient's heart corresponding to the respective node, relative to a reference location on the patient's heart, corresponding to the reference node;

c) determining a measure for heart activation synchronicity for the entire heart based on the relative time delay values of all of the nodes of the plurality of nodes; and determining, by the computer, a patient-specific candidate location for implantation of the pacemaker at the patient's heart, the patient-specific candidate location for implantation of the pacemaker electrode at the patient's heart corresponding to a location of a candidate node in the three-dimensional model selected on the basis of the respective measure for heart activation synchronicity for the entire heart at each node being at least one of (i) a highest synchronicity for at least a subset of the plurality of nodes or (ii) within a predetermined interval; and implanting the pacemaker electrode at the patient's heart at the determined patient-specific candidate location.

2. The method of claim 1, wherein the measure for heart activation synchronicity is one of standard deviation (std) of the depolarization (dep) times of the heart; range in depolarization times; standard deviation of the Left Ventricle (LV) or Right Ventricle (RV) only; delay between stimulus and Septum activation.

3. The method of claim 1, further including defining a common node, wherein for each node the step b) includes determining for each node of the plurality of nodes a value representative of a time delay of electrical activation relative to the node and the common node.

4. The method of claim 3, wherein the common node corresponds to an intrinsic activation site of the heart of the patient or an artificial stimulation site on the heart of the patient.

5. The method of claim 1, further including defining a plurality of common nodes, wherein for each node the step b) includes determining for each node of the plurality of nodes a value representative of a time delay of electrical activation relative to the node and the plurality of common nodes.

6. The method of claim 1, wherein the obtaining of the patient-specific three-dimensional model of the heart includes:
   obtaining a patient-specific three-dimensional geometric model of the heart, and optionally the lungs and/or the thorax;
   obtaining ECG data representative of electric function of the heart;
   on the basis of the three-dimensional geometric model of the heart, and optionally the lungs and the thorax, and the ECG data, determining the patient-specific three-dimensional model of the heart wherein each node of the plurality of nodes has associated therewith the value representative of the time delay of electrical activation of the node relative to an adjacent node of the plurality of nodes.

7. The method of claim 6, wherein the obtaining of the patient-specific three-dimensional geometric model includes:
   obtaining the three-dimensional geometric model from a database including a plurality of different three-dimensional models.

8. The method of claim 7, wherein the three-dimensional geometric models in the database are representative of subjects that differ in at least one of gender, age, weight, body length, chest circumference, frame size, and body-mass-index.

9. The method of claim 7, including the steps of:
   comparing a three-dimensional image of an anatomy of the patient with one or more three dimensional geometric models stored in the database; and
   selecting the three-dimensional geometric model that best corresponds to the three-dimensional image.

10. The method of claim 6, wherein the obtaining of the three-dimensional model of the heart includes:
    recording the exact locations of electrodes of the ECG on the thorax.

11. The method of claim 6, wherein the obtaining of the three-dimensional model of the heart includes:
    relating the measurements per electrode of the ECG to the three-dimensional geometric model of the heart, and optionally the lungs and thorax, and estimating electrical activation of the heart by inverse calculation.

12. The method of claim 1, wherein the obtaining of the three-dimensional model of the heart includes:
    incorporating scar tissue in the three-dimensional model of the heart.

13. The method of claim 1, wherein the obtaining of the three-dimensional model of the heart includes:
    incorporating cardiac blood vessels, such as cardiac veins, in the three-dimensional model of the heart.

14. The method of claim 1, further including:
    on the basis of the respective measure for heart activation synchronicity at each node, determining a node having the highest synchronicity as the candidate node.

15. The method of claim 1, further including obtaining location information of one or more actual pacemaker electrodes at the patient's heart.

16. The method of claim 15, wherein the location information of one or more actual pacemaker electrodes at the patient's heart is obtained from the patient-specific three-dimensional geometric model.

17. The method of claim 3, further including obtaining location information of one or more actual pacemaker electrodes at the patient's heart, and wherein the one or more actual pacemaker electrode locations form the common node, possibly in combination with an intrinsic activation site of the patient's heart.

18. The method of claim 6, wherein the patient-specific three-dimensional geometric model of the heart, and optionally at least one of the lungs or the thorax, is derived from an MRI or computed tomography (CT) image.

19. The method of claim 1, wherein the candidate node is selected as the node having the highest measure for heart activation synchronicity or the highest measure for heart activation synchronicity within a group of nodes associated with cardiac veins.

20. The method of claim 1, wherein if the candidate node is selected as the node having the highest measure for heart activation synchronicity within a group of nodes associated with cardiac veins, it is determined whether the measure for heart activation synchronicity associated with the candidate node is within a predetermined acceptance interval, and if the measure for heart activation synchronicity associated with the candidate node is outside the predetermined acceptance interval, a candidate node having the highest measure for heart activation synchronicity is selected from nodes not associated with cardiac veins.

21. A method for selecting a patient-specific preferred stimulus site of a heart of a patient, including:
    a) obtaining, by a computer, a patient-specific three-dimensional model of the heart of the patient, the patient-specific three-dimensional model including a mesh representing a surface of the myocardium, the mesh having a plurality of nodes, each node having associated therewith a model time delay value representative of a time delay of electrical activation of the node relative to a predetermined node of the plurality of nodes;
    b) defining, by the computer in the model a candidate node at a node of the patient-specific three-dimensional model of the heart;
    c) on the basis of the three-dimensional model of the heart and the defined candidate node determining, by the computer, a modified three-dimensional model of the heart in which each node of the plurality of nodes has associated therewith a relative time delay value representative of a time delay of electrical activation relative to the candidate node;
    d) repeating the steps b) and c) for a plurality of candidate nodes thereby obtaining modified three dimensional models of the heart;
    (e) comparing, by the computer, the obtained modified three dimensional models of the heart to identify a particular candidate node associated with the modified three dimensional model of the heart having at least one of (i) a highest synchronicity for at least a subset of the plurality of nodes or (ii) having a synchronicity within a predetermined interval; and selecting, by the computer, a preferred stimulus site of the patient corresponding to the particular node; and implanting a pacemaker electrode at the selected preferred stimulus site on the heart of the patient.

* * * * *